United States Patent [19]
Evans et al.

[11] Patent Number: 5,965,330
[45] Date of Patent: *Oct. 12, 1999

[54] METHODS FOR FABRICATING ANNULAR MASK LENS HAVING DIFFRACTION-REDUCING EDGES

[75] Inventors: John M. Evans, Fremont; Chun-Shen Lee, Cupertino; Praful C. Doshi, Poway; Jerome A. Legerton, Los Gatos, all of Calif.

[73] Assignee: PBH, Inc., Des Plaines, Ill.

[*] Notice: This patent is subject to a terminal disclaimer.

[21] Appl. No.: 08/761,308

[22] Filed: Dec. 6, 1996

[51] Int. Cl.⁶ ........................................... G02C 7/04
[52] U.S. Cl. .............................. 430/321; 430/5; 351/162; 351/165; 351/177
[58] Field of Search .................. 351/161, 162, 351/165, 177; 430/5, 320, 321

[56] References Cited

U.S. PATENT DOCUMENTS

| | | | |
|---|---|---|---|
| 3,339,997 | 9/1967 | Wesley | 351/161 |
| 3,946,982 | 3/1976 | Calkins et al. | 249/102 |
| 4,666,249 | 5/1987 | Bauman et al. | 351/160 H |
| 4,672,021 | 6/1987 | Blumel et al. | 430/312 |
| 4,702,574 | 10/1987 | Bawa | 351/162 |
| 4,849,323 | 7/1989 | Endo et al. | 430/312 |
| 4,889,795 | 12/1989 | Kaifu et al. | 430/326 |
| 4,994,080 | 2/1991 | Shepard | 623/5 |
| 5,089,024 | 2/1992 | Christie et al. | 623/6 |
| 5,108,169 | 4/1992 | Mandell | 351/161 |
| 5,172,143 | 12/1992 | Baude et al. | 351/177 |
| 5,260,727 | 11/1993 | Oksman et al. | 351/162 |
| 5,296,305 | 3/1994 | Baude et al. | 427/164 |
| 5,302,978 | 4/1994 | Evans et al. | 351/162 |
| 5,414,477 | 5/1995 | Jahnke | 351/162 |
| 5,516,467 | 5/1996 | Niwa et al. | 264/1.1 |
| 5,643,249 | 7/1997 | Amano et al. | 606/4 |
| 5,662,706 | 9/1997 | Legerton et al. | 351/162 |

FOREIGN PATENT DOCUMENTS

| | | |
|---|---|---|
| 241 330 | 12/1992 | Argentina . |
| 244 890 | 11/1993 | Argentina . |
| 0 225 098 | 6/1987 | European Pat. Off. . |
| 1115140 | 12/1955 | France . |
| 1400566 | 4/1965 | France . |
| 2599-156 | 5/1986 | France . |
| 03-1857 | 1/1991 | Japan . |
| 07-050242 | 2/1995 | Japan . |
| 1276003 | 6/1972 | United Kingdom . |
| 1 547 525 | 6/1979 | United Kingdom . |
| WO 94/23327 | 10/1994 | WIPO . |
| WO97/48004 | 12/1997 | WIPO . |

OTHER PUBLICATIONS

Bailey, O.D., Ph.D., Special Contact Lenses and Their Applications, pp. 32–33, Optical Journal–Review, Jan. 1, 1960.

Contact Lens Practice, pp. 394–398, 644, 646, 655–656.

Groppi, New Aspects in the Fitting of the Multi–Range Bifocal Contact Lens, Contacto, 15(2):22–29 (1971).

Mazow, The Pupilens—A Preliminary Report, International Contact Lens Congress in Munich, Aug. (1958).

Neefe, Neefe Special Contact Lenses, Contacto, Nov. (1975).

Rosenbloom, The Controlled–Pupil Contact Lens in Low Vision Problems, Journal of the American Optometric Association 40(8):836–840 (1969).

Wesley, *A New Concept in Successful Bifocal Contact Lens Fitting*, pp. 71–73.

*Primary Examiner*—Martin Angebrannt
*Attorney, Agent, or Firm*—Burns, Doane, Swecker & Mathis, L.L.P.

[57] ABSTRACT

Methods for fabricating annular mask lens for vision correction having diffraction-reducing edges are provided. The lens body having an annular mask that forms a "soft edge" by gradually decreasing the transmissivity radially from the center aperture to the annular mask area. The methods introduce varying levels of a coloring agent (e.g., dye) into certain portions of the lens.

19 Claims, 14 Drawing Sheets

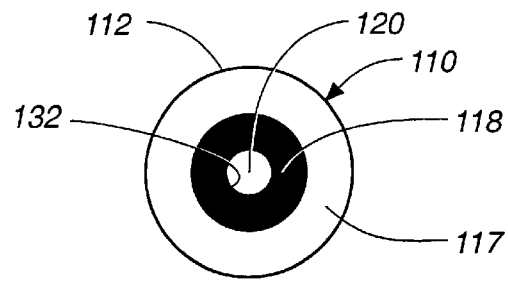
FIG._1A
(PRIOR ART)
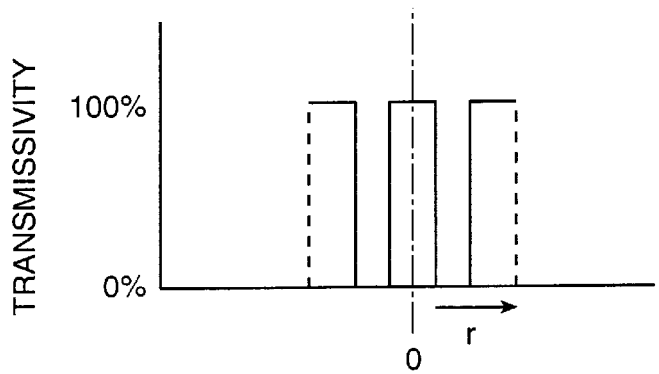
FIG._1B
(PRIOR ART)
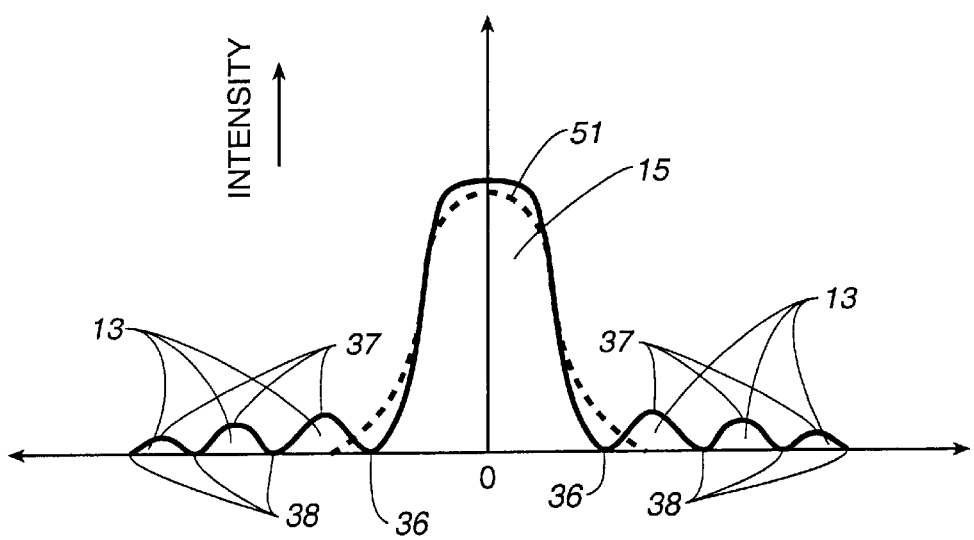
FIG._2

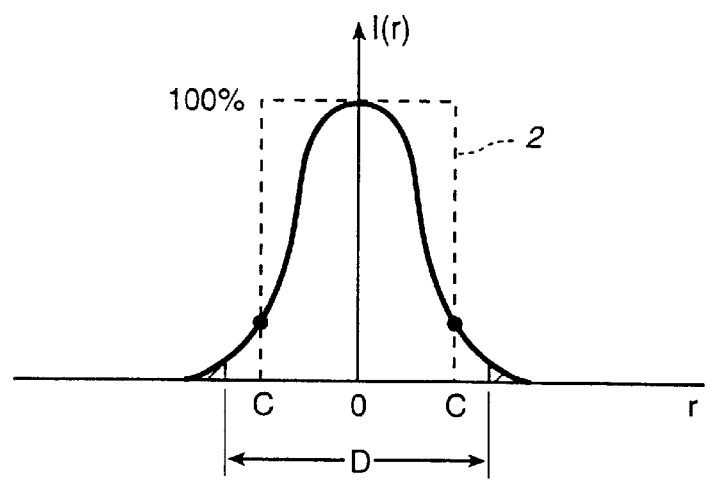
FIG._3
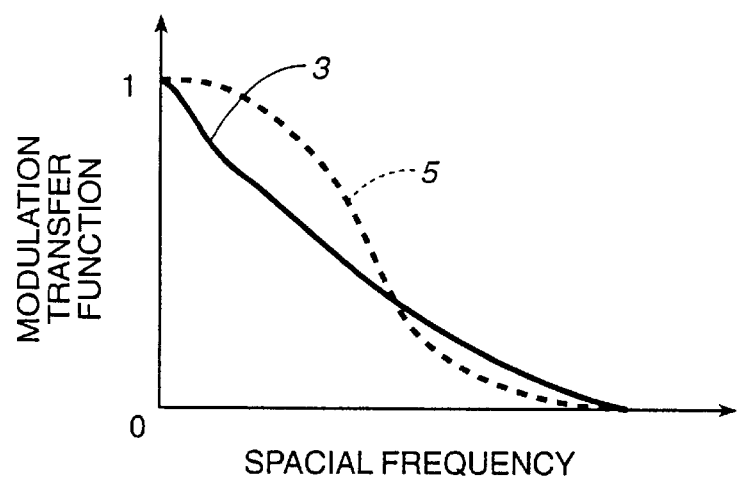
FIG._4
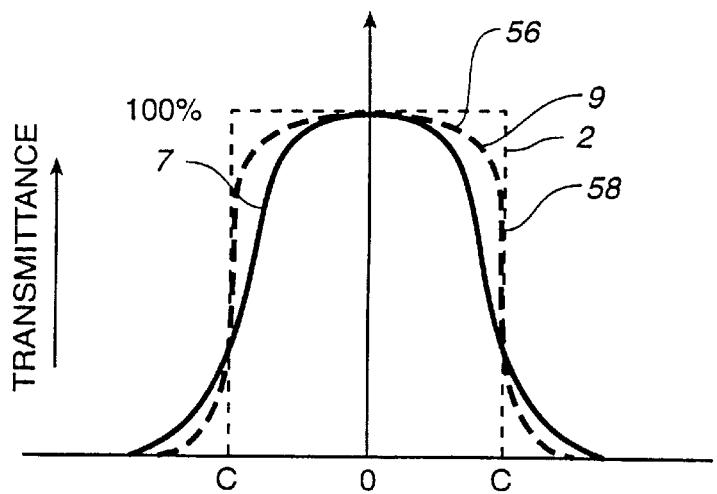
FIG._5

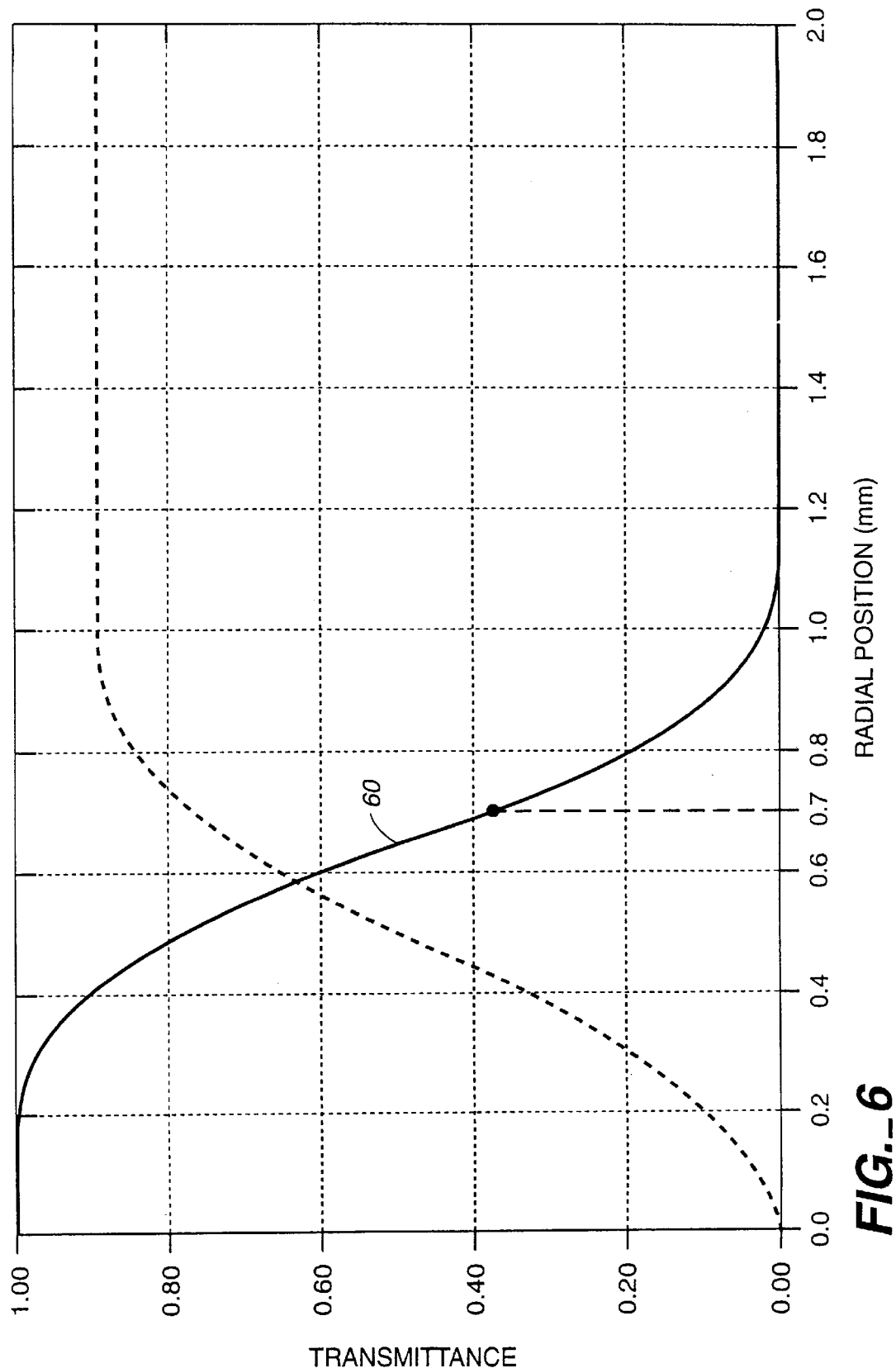
FIG._6

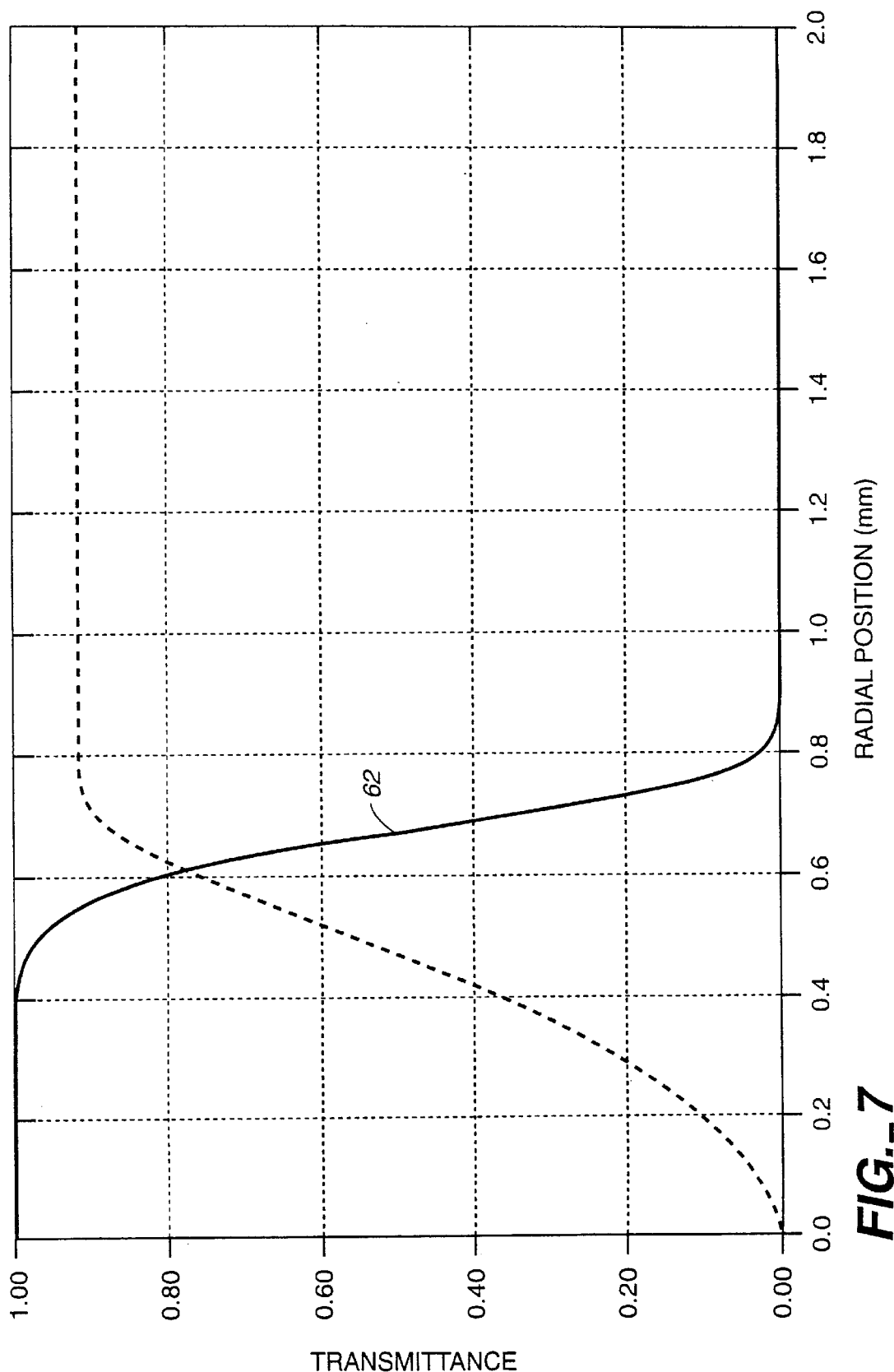
FIG._7

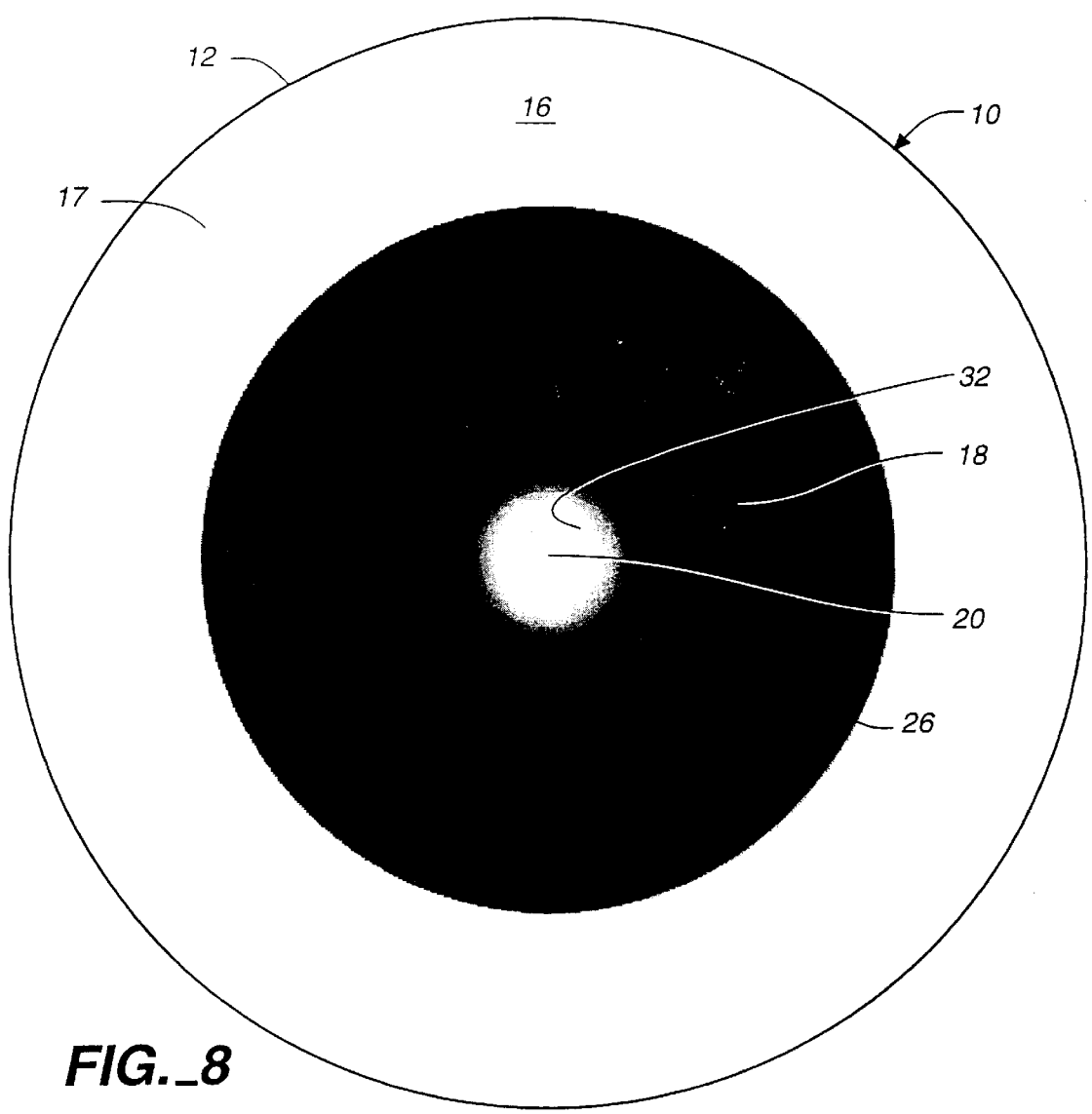
FIG._8

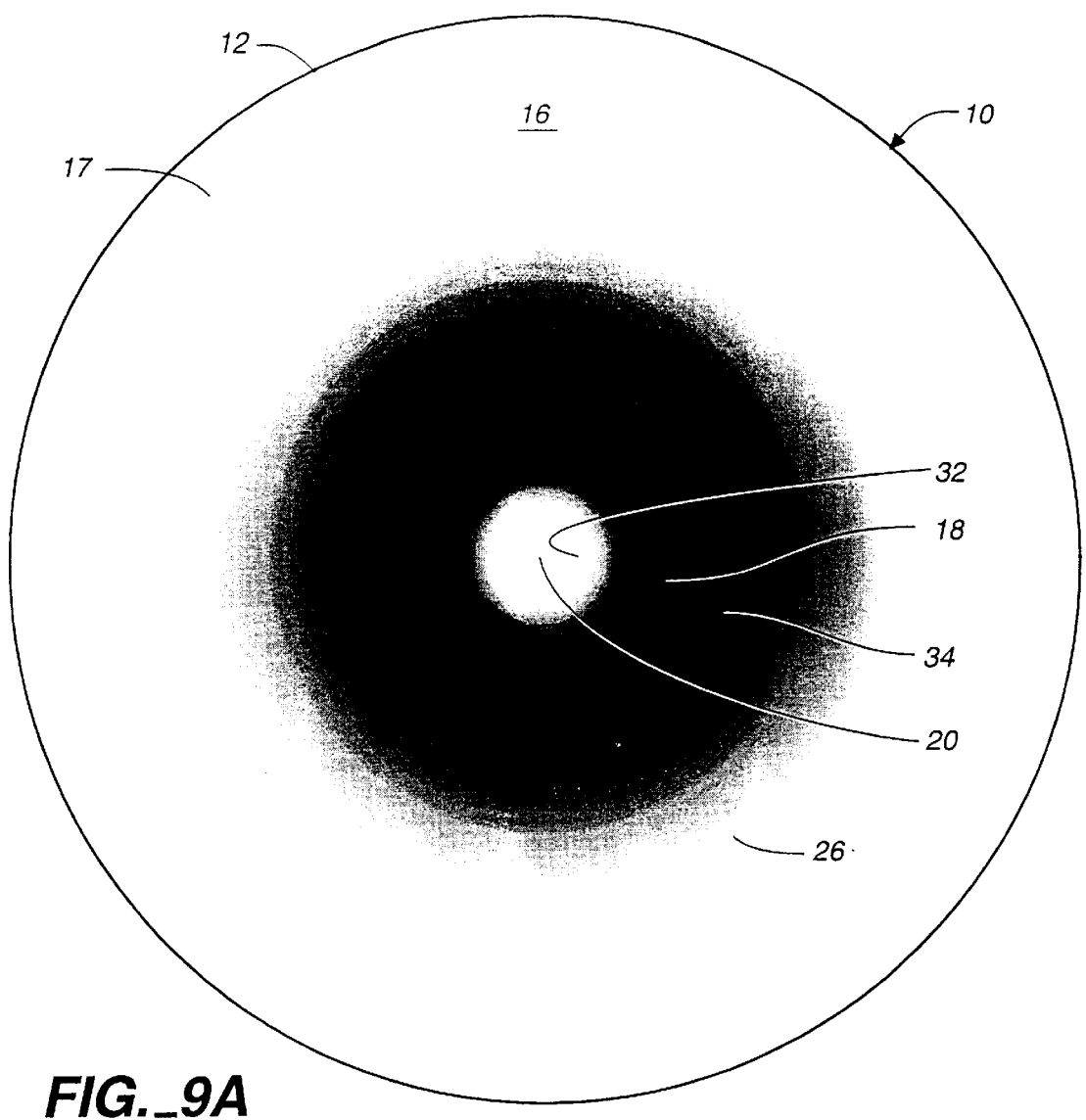
FIG._9A

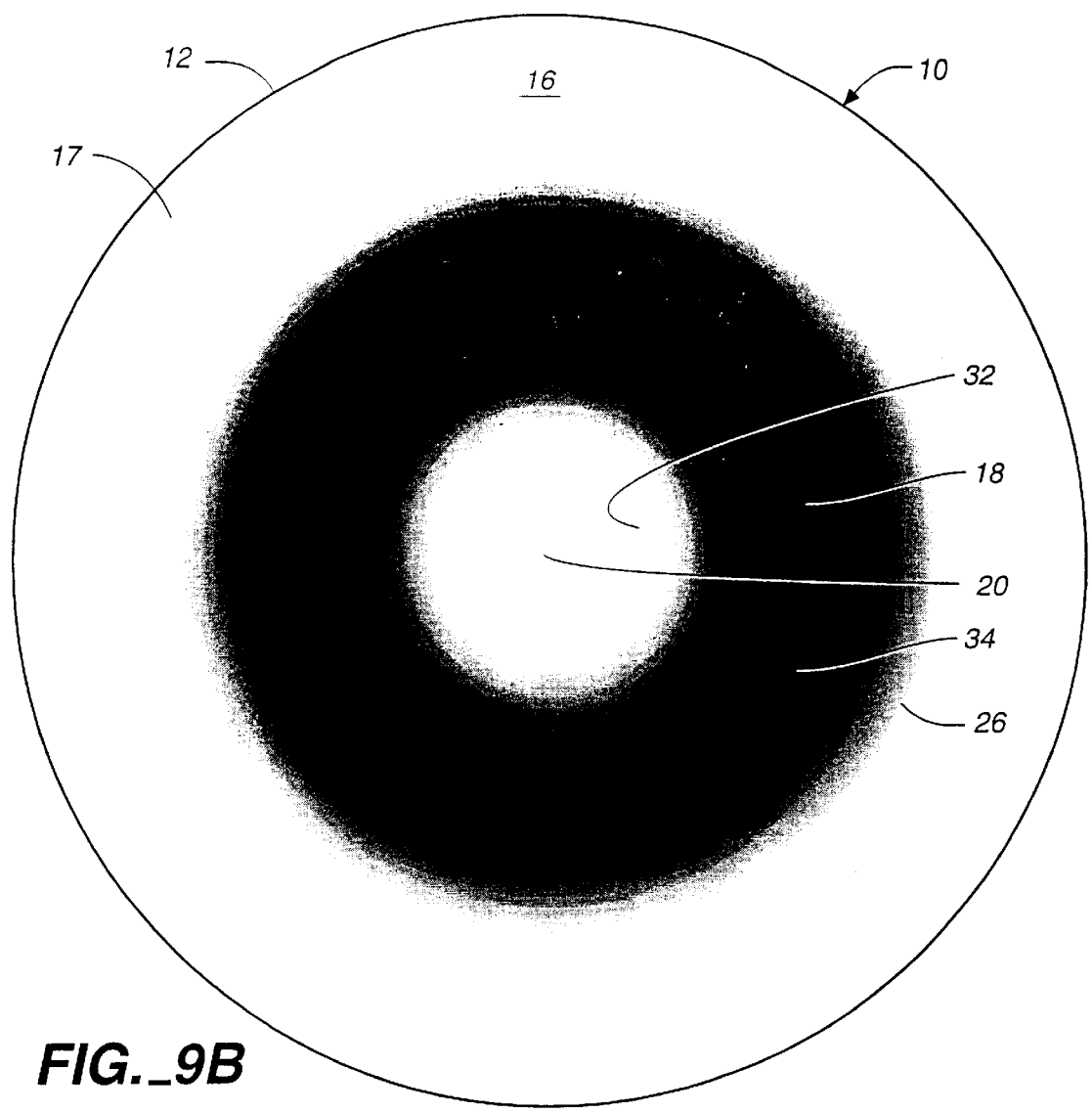
FIG._9B

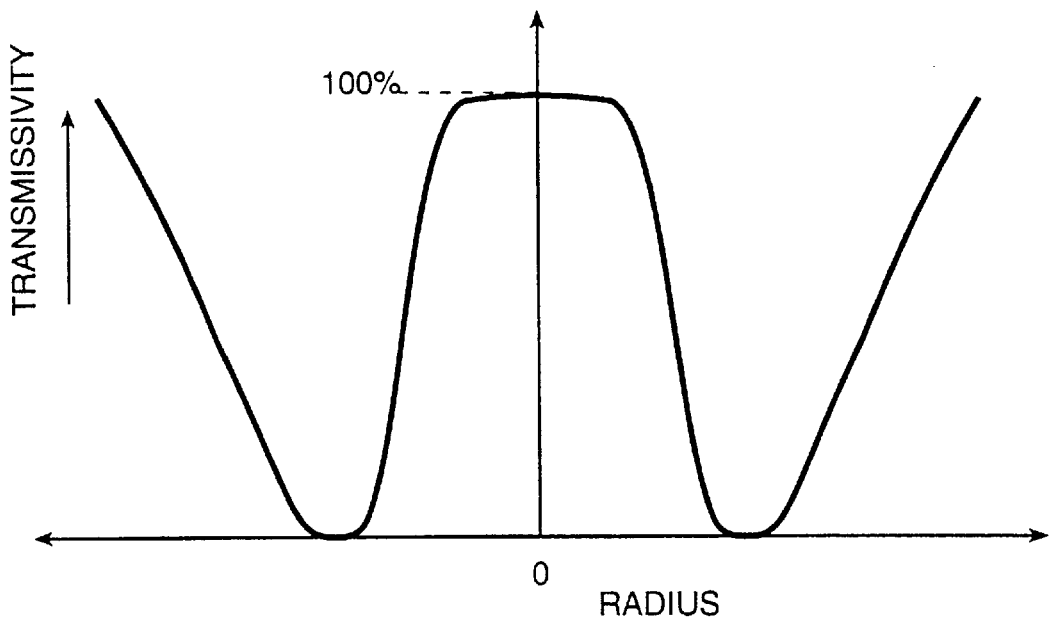
FIG._10
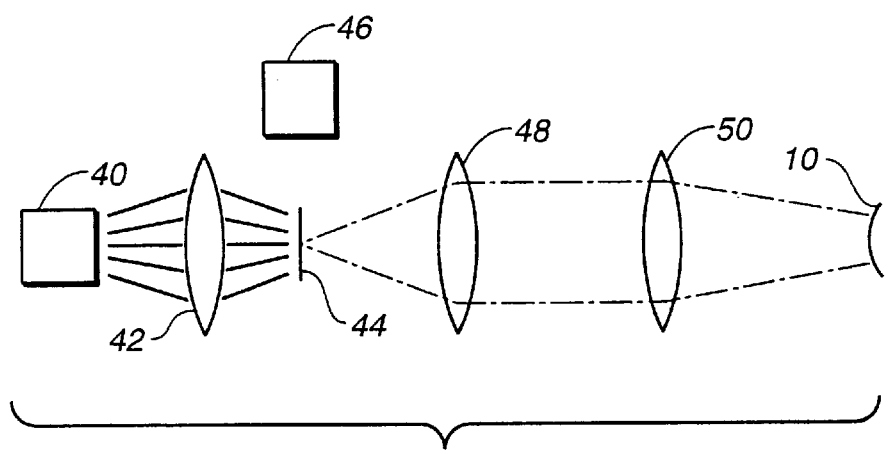
FIG._12

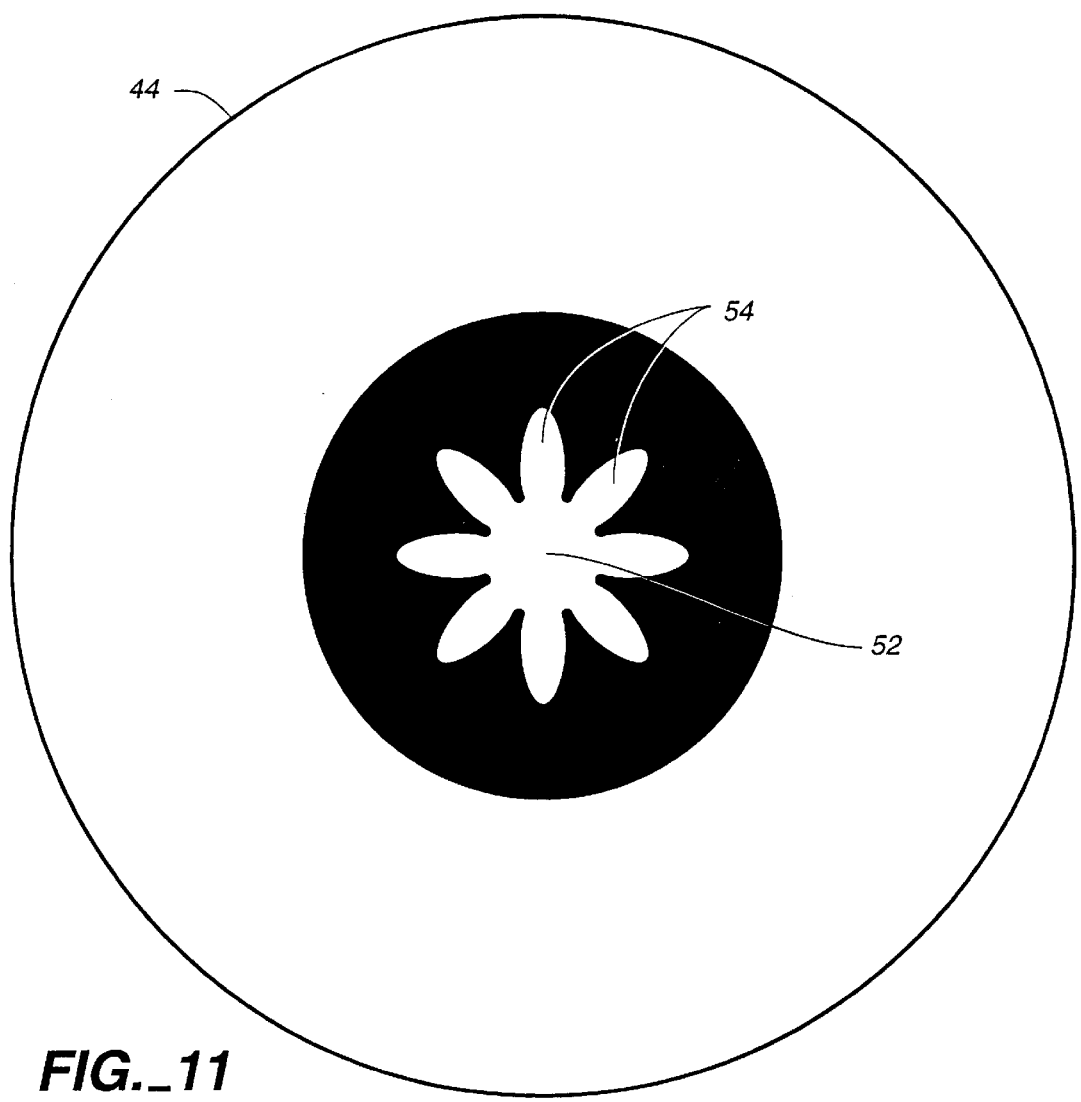
FIG._11

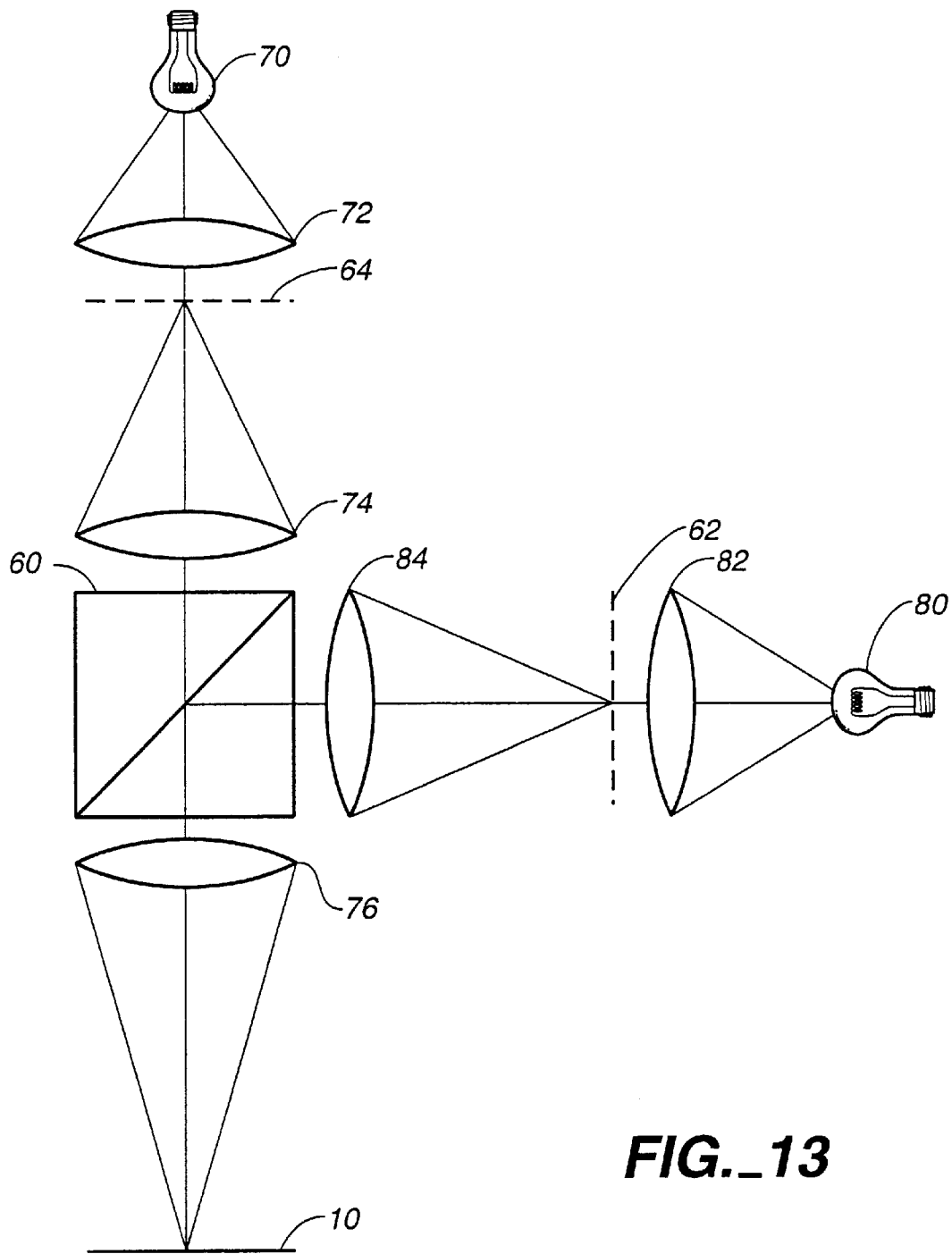
FIG._13

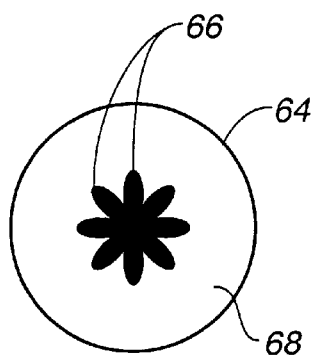
FIG._14A
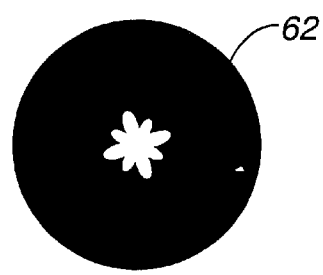
FIG._14B
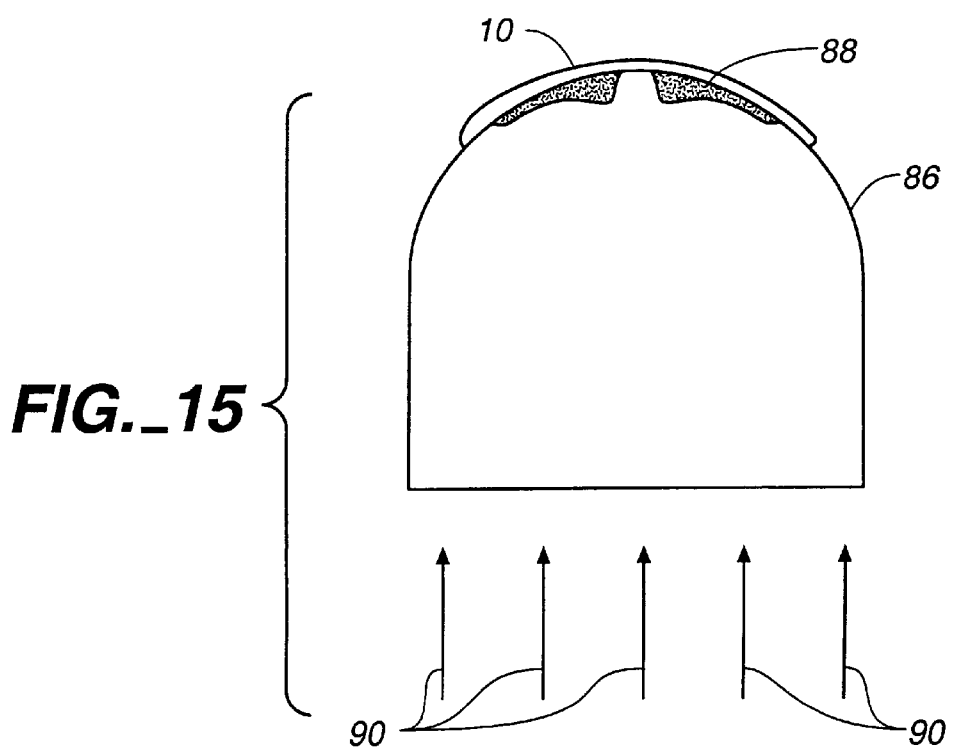
FIG._15

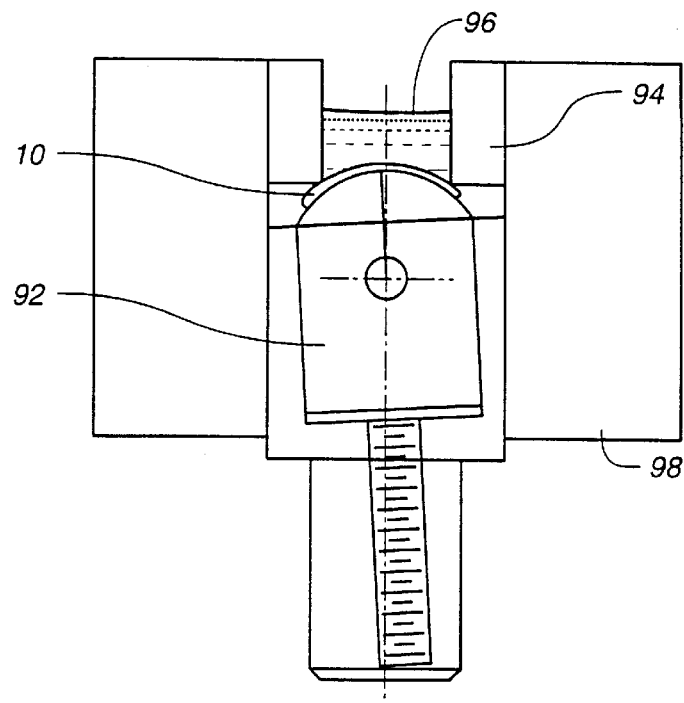
FIG._16
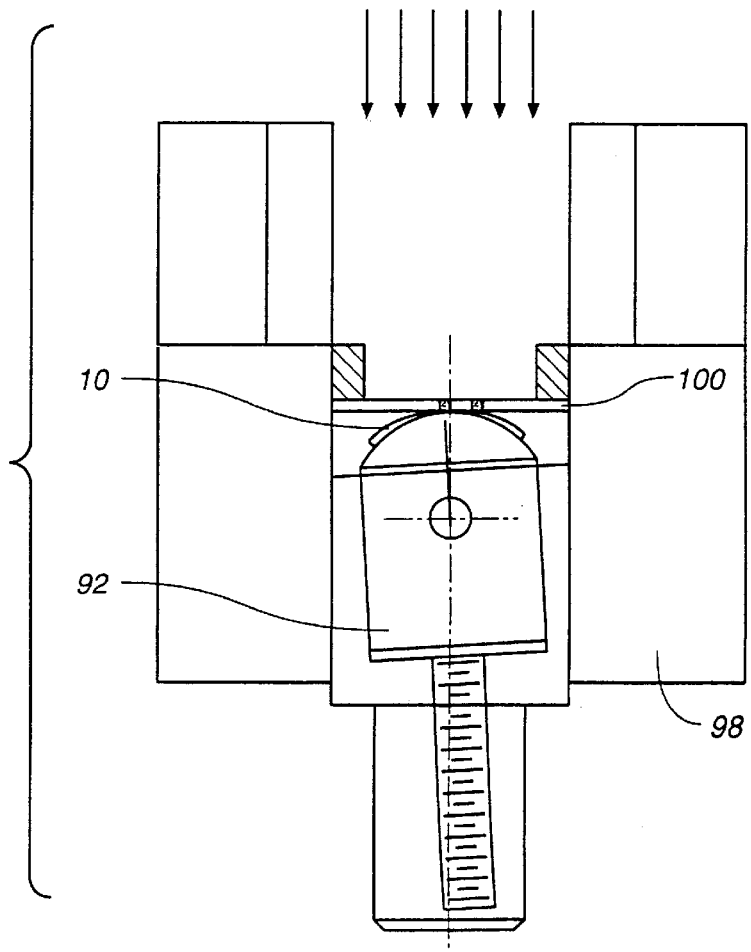
FIG._17

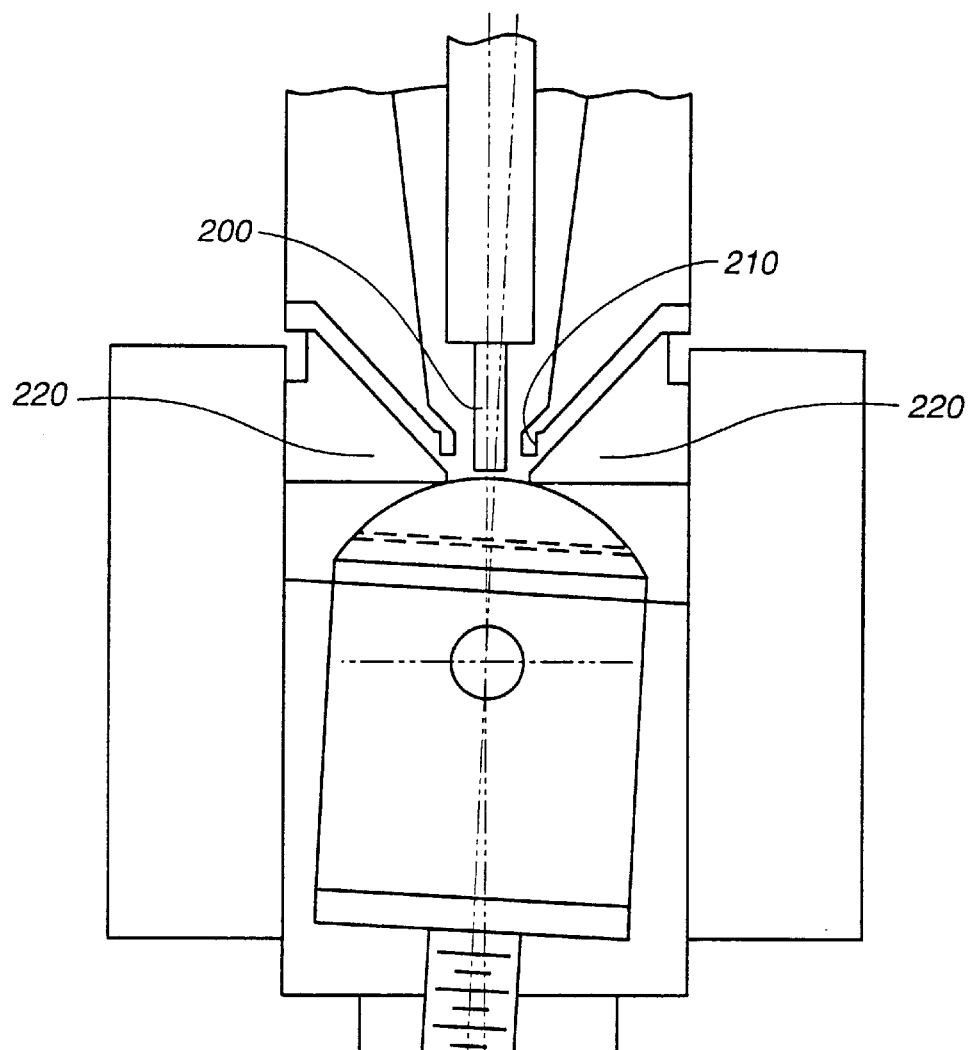
FIG._18

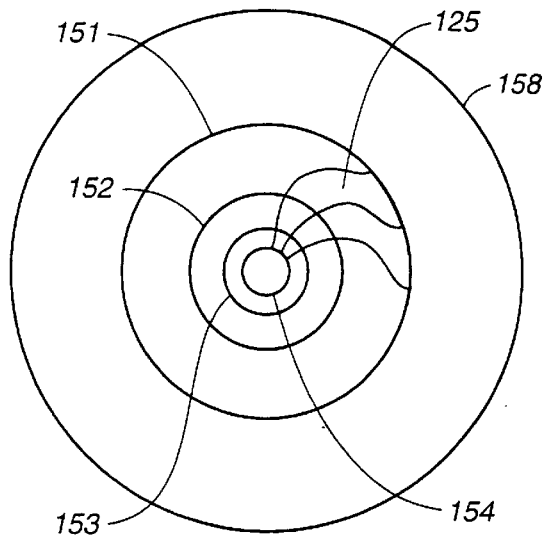
FIG._19A
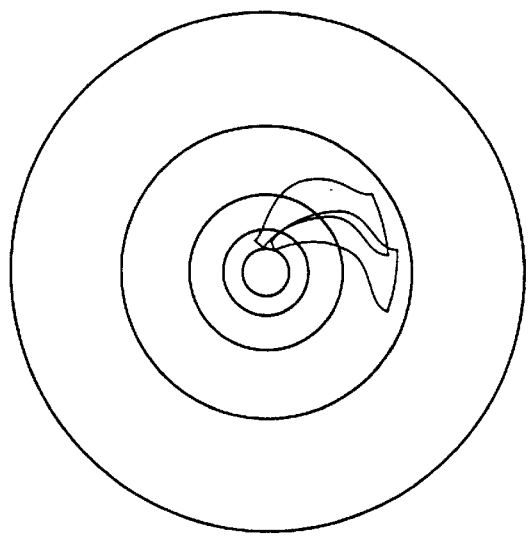
FIG._19B
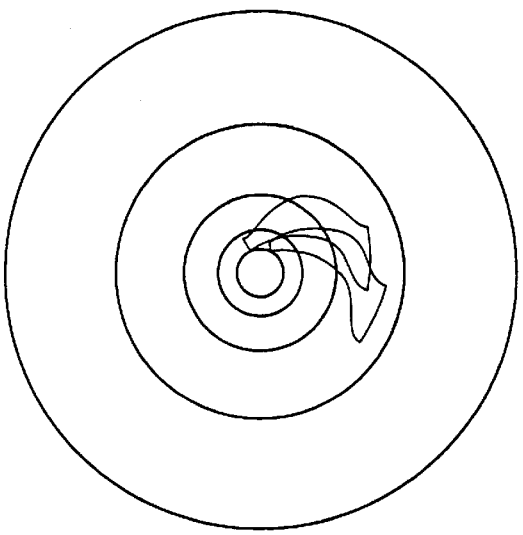
FIG._19C
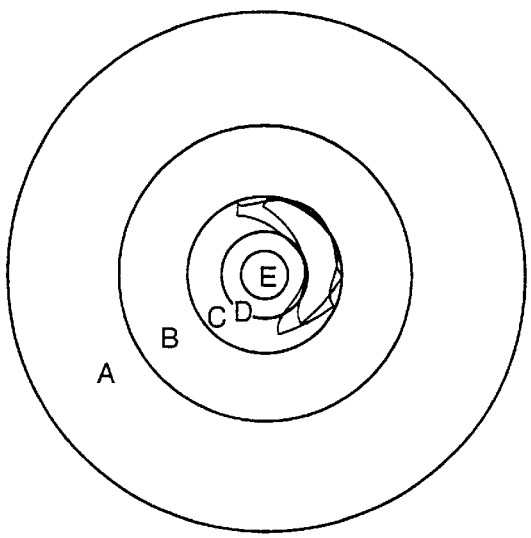
FIG._19D

METHODS FOR FABRICATING ANNULAR MASK LENS HAVING DIFFRACTION-REDUCING EDGES

FIELD OF THE INVENTION

This invention concerns a lens for vision correction and, in particular, masked lenses and related methodology.

BACKGROUND OF THE INVENTION

Contact lenses are commonplace today. Most individuals with average refractive errors can quickly and easily acquire and use these lenses in place of prescription eye glasses. This is not true, however, for individuals who are presbyopic (i.e., those requiring multi-focal visual correction) or for those individuals with structural eye abnormalities. These individuals are left with little choice in selecting comfortable, effective contact lenses. Lenses which are available typically encumber these wearers with other difficulties, and are usually very expensive. Presbyopic individuals, for example, who choose to wear soft contact lenses are usually fitted in a "monovision" mode, where one eye is corrected for near vision, and the other eye is corrected for far vision. Notwithstanding the availability of multifocal lenses, such lenses are not versatile in supplying simultaneous clear distance/near vision and are not commercially successful.

The long felt need to develop more versatile multifocal lenses has led designers to "pinhole" contact lenses (e.g., PCT Publication No. WO95/08135 published Mar. 23, 1995). These lenses endeavor to utilize the known theories of pinhole imaging as a method to reduce or eliminate visual deficiencies. An annular mask with a clear center aperture of various sizes (conventionally up to 4 mm in diameter) is used to increase the depth of focus of presbyopic individuals. Unfortunately, the conventional pinhole contact lenses have been ineffective in part because they suffer from diffraction effects at the sharp demarcation where the pinhole aperture stops and the opaque mask surrounding the aperture begins.

There has also been a long felt need for treatment of patients with optical aberration problems, for example, night myopia, which is an increase in refractive error due to the dilation of the pupil and the effect of spherical aberration. Also, increased spherical aberration in patients having radial keratotomy and photo-refractive keratectomy due to prolate geometry of the cornea following surgery and aberrations due to corneal distortion and scarring resulting from trauma or genetic conditions including keratoconus. Conventional pinhole contact lens cannot adequately address these problems because the loss of retinal illumination due to the pinhole aperture offsets the peripheral distortion benefit.

"Multiple Focal Contact Lenses", as described in U.S. Pat. No. 3,794,414, was one attempt to develop small-aperture contact lenses. This approach combined a pinhole-like aperture with radial slits and scalloped masking regions on a contact lens supposedly to correct both peripheral vision and the effects related to decentered contact lenses. The masked contact lenses were made from a rigid substrate, and "floated" on the eye, creating a need for apertures over a large portion of the lens. The disclosed designs though (i.e., the use of scalloped patterns and radial slits) actually encourage diffraction effects at the retina. This reduces image quality. The purpose of pinhole aperture correction is to correct geometrical aberrations in excess of diffraction. Therefore, the benefits achieved according to that patent by incorporating the pinhole aperture, are likely to be offset by undesirable diffraction effects.

Pinhole correction together with the normal functioning of the human pupil is considered in U.S. Pat. No. 4,955,904, which presents a masked intraocular lens surgically implanted within the eye. The patent, entitled "Masked Intraocular Lens and Method for Treating a Wearer With Cataracts", affords cataract wearers some form of vision correction through surgery. The intraocular lens is masked to form a pinhole that accommodates the function of the human pupil under different lighting conditions. However, the intraocular lens of that patent is also likely to be offset by undesirable diffraction effects created by the sharp demarcation at the junction of the pinhole and the opaque mask. U.S. Pat. No. 5,245,367 issued to Miller et al. discloses an annular mask contact lens wherein the optical opacity of the mask region can vary within the lens.

SUMMARY OF THE INVENTION

The present invention provides methods of fabricating lenses having an annular mask which eliminates the sharp demarcation at the edge of the conventional pinhole and non-pinhole apertures.

The inventive method can fabricate a lens body that has a mask that forms a "soft edge" by gradually decreasing the transmissivity radially from the center aperture to the masked area. The improved mask eliminates the "halo effect" associated with conventional annular masks by eliminating or reducing diffraction around the outer edge of the mask. The inventive lens body has a mask that gradually increases the transmissivity radially again toward the outer edge of the mask. The advantages of these lens are several. The lens improves a wearer's vision over a wide range of viewing distances. The lens reduces and/or eliminates diffraction effects associated with a conventional pinhole lens. The lens improves a wearer's vision during differing brightness conditions by incorporating the normal function of the human pupil into the transmissivity of the annular mask. Moreover, a multi-powered lens can also be fabricated.

The inventive method can also fabricate non-pinhole contact lenses having a transparent lens body with an annular mask which gradually increases in transmissivity radially and which defines an aperture whose diameter is of sufficient size so as not to be effective as or a substitute for refractive correction, that is, the aperture does not provide pinhole effect correction (i.e., refractive substitute correction for myopia, presbyopia, hyperopia, and other conditions). The annular mask can reduce or eliminate the effects of night myopia, spherical aberration (i.e., "halos"), aniridia, keratoconus, corneal scaring, penetrating keratoplasty or post refractive surgery complications (among others) by utilizing an annular mask having a "soft" inside edge and that gradually increases the transmissivity radially toward the outer edge of the mask.

In a first aspect, the invention is directed to a method of fabricating a lens adapted to be worn on or implanted in the eye wherein the lens includes regions having different levels of visible light transmissivity, that includes the steps of:

a. positioning a lens substrate onto a surface of a substrate support wherein a photosensitive reagent is present on a lens substrate surface and/or in the lens substrate;

b. positioning a mask having radiation restricting regions over a surface of the lens substrate;

c. directing radiation toward the mask so that radiation passes through the mask and onto the lens substrate; and d. exposing the lens substrate to sufficient radiation to interact with the photosensitive reagent.

In a second aspect, the invention is directed to a method of fabricating a lens adapted to be worn on or implanted in the eye wherein the lens includes regions having different levels of visible light transmissivity, that includes the steps of:

a. positioning a lens substrate onto a first surface of a substrate support wherein a photosensitive reagent is present on a lens substrate surface and/or in the lens surface and wherein the second surface of the support comprises radiation restricting regions;
 b. directing radiation through the second surface of the support and onto the lens substrate; and
 c. exposing the lens substrate to sufficient radiation to cause the photosensitive reagent to react.

In a third aspect, the invention is directed to a method of fabricating a lens adapted to be worn on or implanted in the eye wherein the lens includes regions having different levels of visible light transmissivity, that includes the steps of:

a. positioning a lens substrate onto a first surface of a substrate support;
 b. placing a center dam, an inner ring, and an outer ring on a surface of the lens surface, wherein the center dam and the inner ring forms a first annular region on a surface of the lens and the inner ring and outer ring defines a second annular region on a surface of the lens;
 c. placing a solution containing a dye or pigment onto the first region and allow some of the dye or pigment to diffuse into the lens defined by the first region; and, thereafter
 d. lifting the inner ring from said surface and allowing the solution to flow onto the second region and allow some of the dye or pigment to diffuse into the lens defined by the second region.

In a fourth aspect, the invention is directed a method of fabricating a lens adapted to be worn on or implanted in the eye wherein the lens includes regions having different levels of visible light transmissivity, that includes the steps of:

a. providing a lens substrate that has a photosensitive reagent present on the lens substrate surface or in the lens substrate;
 b. positioning a mask having radiation restricting regions over a surface of the lens substrate;
 c. providing a source of radiation and directing radiation through the mask and onto the lens substrate; and
 d. exposing the lens substrate to sufficient radiation to interact with the photosensitive reagent.

In a fifth aspect, the invention is directed to a method of fabricating a lens adapted to be worn on or implanted in the eye wherein the lens includes regions having different levels of visible light transmissivity, that includes the steps of:

a. providing a lens substrate that has a photosensitive reagent present on a lens substrate surface or in the lens surface;
 b. providing a first source of radiation and positioning adjacent to said first source a first mask having first radiation restricting regions;
 c. providing a second source of radiation and positioning adjacent to said second source a second mask having second radiation restricting regions;
 d. focusing radiation from the first source onto the lens substrate whereby the radiation travels through the first mask;
 e. focusing radiation from the second source onto the lens substrate whereby the radiation travels through the second mask; and
 f. exposing the lens substrate to sufficient radiation to react with the photosensitive reagent.

In a preferred embodiment, the method further comprises rotating one or both of said first and second masks. In addition, or alternatively, the method comprises of spinning the lens.

In a sixth aspect, the invention is directed to a method of fabricating a lens adapted to be worn on or implanted in the eye wherein the lens includes regions having different levels of visible light transmissivity, that includes the steps of:

a. providing a lens substrate that has a photosensitive reagent present on the lens substrate surface, in a lens substrate or both the lens substrate surface and the lens substrate;
 b. providing a source of radiation;
 c. positioning a shutter masking device between the source of radiation and said lens surface; and
 d. opening a shutter window in the device from a first position to second position as radiation is directed onto the surface of the substrate through the window thereby exposing a surface of the lens substrate to varying levels of radiation and causing the photosensitive reagent to react and produce a light transmissivity gradient in said lens substrate.

In a seventh aspect, the invention is directed to a method of fabricating a lens adapted to be worn on or implanted in the eye wherein the lens includes regions having different levels of visible light transmissivity, that includes the steps of:

a. providing a lens substrate that has a photosensitive reagent present on the lens substrate surface, in a lens substrate or both the lens substrate surface and the lens substrate;
 b. providing a source of radiation;
 c. positioning a shutter masking device between the source of radiation and said lens surface;
 d. directing radiation towards the device; and
 e. closing a shutter window in the device from a first position to second position as radiation is directed onto the surface of the substrate through the window thereby exposing a surface of the lens substrate to varying levels of radiation and causing the photosensitive reagent to react and produce a light transmissivity gradient in said lens substrate.

In one preferred embodiment, lens that is fabricated has a substantially transparent central portion that has a center which is offset from the geometric center of the lens. In another preferred embodiment, the center of the substantially transparent central portion is offset by a distance of about 0 mm to 1.5 mm from the geometric center. Depending on the particular process, the photosensitive reagent may comprise, for example, photoreactive dyes or diazo dyes.

In another embodiment, the lens that is produced has a central portion having selected transmissivity such that the central portion transmits more light energy at the center of the central portion and less light energy toward an outer region and annular mask region surrounding the central portion. Preferably, the central portion has a diameter of sufficient size so as not to be effective as or a substitute for refractive correction.

In another embodiment, the lens formed has a clear aperture, an annular region adjacent to the clear aperture which transmits more light energy at an inner region and less light energy toward an outer region, and an annular mask region surrounding the outer portion of the annular portion. In one embodiment, the aperture has a diameter of sufficient size so as not to be effective as or a substitute for refractive correction. In an alternative embodiment, the diameter is small enough to provide refractive correction.

BRIEF DESCRIPTION OF THE DRAWINGS

FIG. 1A is a plan view of an annular mask contact lens constructed in accordance with the prior art;

FIG. 1B is a graph that illustrates the transmissivity of the lens of FIG. 1A;

FIG. 2 illustrates the point spread function of a point object imaged through a circular aperture;

FIG. 3 illustrates the transmittance of a Gaussian apodized aperture in accordance with one embodiment of the present invention;

FIG. 4 is a comparison of the perfect lens modulation transfer function of a uniform aperture and the modulation transfer function of a truncated Gaussian apodized aperture with respect to spatial frequency;

FIG. 5 is a comparison of the transmittance of a uniform aperture, Gaussian apodized aperture and pseudo-Gaussian apodized aperture;

FIG. 6 is a graph of transmittance versus radial position for a pseudo-Gaussian apodized aperture in accordance with one embodiment of the present invention;

FIG. 7 is a graph of transmittance versus radial position for a pseudo-Gaussian apodized aperture in accordance with one embodiment of the present invention;

FIG. 8 is a rendition from a photograph of an annular mask in accordance with one embodiment of the present invention with the perimeter of the lens shown by a solid line;

FIGS. 9A and 9B are each a rendition from a photograph of an annular mask in accordance with another embodiment of the present invention with the perimeter of the lens shown by a solid line;

FIG. 10 is a graph of transmittance versus radial position for the annular mask of FIG. 9A;

FIG. 11 is one embodiment of a mask pattern used to produce the annular mask of FIG. 8;

FIG. 12 is a diagrammatic representation of an apparatus used to produce the annular mask of FIG. 8;

FIG. 13 is a diagrammatic representation of an apparatus used to produce the annular mask of FIGS. 9A and 9B;

FIGS. 14A AND 14B are plan views of a set of masks used in the apparatus of FIG. 13;

FIG. 15 is an apparatus for use in another method for producing the present invention;

FIGS. 16, 17, and 18 illustrate a device that is particularly suited for producing lens that are offset; and FIGS. 19A, 19B, 19C, and 19D depicts a device having a shutter system used to produce a mask on a lens.

DESCRIPTION OF THE PREFERRED EMBODIMENTS

The present invention will now be described with respect to fabricating a contact lens, but as will be appreciated by one of ordinary skill in the art, the principles of the present invention can be incorporated into making any vision correcting lens, including but not limited to contact lenses (including rigid or hard lenses, hybrid lenses, hydrogel lenses and gel lenses that do or do not contain water), intraocular lenses, intracorneal lenses, and anterior chamber lenses. Suitable contact lens fabricated by this invention are further described in U.S. patent application Ser. No. 08/663, 622 entitled "Variable Transmissivity Annular Mask Lens For Treatment of Optical Aberrations" now U.S. Pat. No. 5,662,706 and Ser. No. 08/663,907, entitled "Annular Mask Lens Having Diffraction-Reducing Edges", both filed on Jun. 14, 1996 and which are incorporated herein.

Prior Art Lens

The annular mask 118 used in a conventional pinhole contact lens 110 (FIG. 1A) for presbyopic individuals has a sharp demarcation at the edge 132 of the clear central aperture 120. The graph in FIG. 1B illustrates that the lens body 112 has a transmissivity of 100% in the aperture 120 and in the annular region 117, and no light transmission through the opaque annular mask 118. It is known that the point spread function of a point object imaged through an optical system having a circular aperture (like a conventional pinhole contact lens) has a bright central area known as an Airy Disk 15 and several annuli lobes 13 of lower brightness as depicted in FIG. 2. The intensity is at a maximum at the center of the Airy Disk 15 and decreases to a first dark ring 36. The intensity then increases and decreases infinitely radially outward with exponentially smaller and smaller peaks in the lobes 13. These cycles form several annuli peaks 37 and dark rings 38. The angular radius of the first dark ring 36 at the edge of the Airy Disk 15 is defined by the wavelength of the light and the diameter of the circular aperture that the object is being imaged through. The maximum spatial frequency of an object that can be resolved by an optical system having a circular aperture is limited by the size of the Airy Disk 15 of the point spread function. In a contact lens, the maximum spatial frequency that is resolved is related to the visual acuity. The "side-lobes" or annuli lobes 13 of the point spread function will generally reduce the contrast (i.e., the modulation transfer function) of the image making it more difficult to discern detail. It is known that the "side-lobe" annuli 13 result from the diffraction of light as it passes the sharp edge 132 (i.e., abrupt demarcation) of the aperture 120. Therefore, eliminating or reducing the abrupt change eliminates or reduces the intensity of the "side-lobe" annuli which enhances the contrast of the image.

Design of Annular Mask Lens with Diffraction Reducing Edges

In its simplest form, the present invention produces a contact lens that utilizes a "soft edge" at the junction of the clear aperture and the annular mask. In one embodiment, this is accomplished by reducing the transmittance of the central aperture as a function of increasing radial position. In another embodiment, this is accomplished by decreasing the transmissivity of the annular mask as a function of increasing radial position.

One method of eliminating the sharp edge (i.e., abrupt demarcation) is by apodizing the aperture. Apodization is the process of changing the energy distribution of the point spread function by deliberate manipulation of the aperture function so as to improve image quality. In other words, the characteristics of the aperture are changed to improve the contrast. The present invention utilizes amplitude apodization such that the amplitude transmittance aperture function varies from the center to the edge of the aperture. FIG. 3 graphically illustrates this embodiment. The transmittance starts at 100% at the center of the lens and decreases as the radial position on the lens increases into the annular mask region. The transmittance function of the aperture 20 of lens 10 (FIG. 8) is, in one embodiment, a Gaussian apodized aperture described by the function (I):

$$I(r) = e^{-(\frac{r}{c})^2}$$

where I(r) is the transmissivity amplitude for the aperture 20 as a function of the radial position, r, and c is the effective radius of the aperture (FIG. 3). For the Gaussian curve defined by the above equation when the transmissivity is 36.8% then the distance to that point defines the effective radius. The effective radius is chosen from the range of radii of a conventional pinhole contact lens (typically about 0.25 to about 1.5 mm) so that the total energy transmitted through the apodized aperture is approximately equal to the total energy transmitted through a conventional pinhole aperture having a radius equal to the effective radius. Preferably, c is 0.7 mm. Curve 2 represents the transmissivity of a conventional pinhole contact lens. One advantage of the Gaussian apodized aperture is that it suppresses or even completely eliminates all of the side-lobe annuli 13 depending on the truncated width, D, of the Gaussian profile. The larger the truncated width, the greater the suppression of the side-lobe annuli. The truncated width is the point at which the annular mask 15 (FIG. 8) begins to function effectively as opaque. Preferably, at a transmissivity of about 1% or less the annular mask is opaque.

There are two significant effects on the point spread function as a result of Gaussian apodization. First, the side-lobe annuli of the point spread function are greatly suppressed or eliminated compared to a uniform (or unapodized) conventional pinhole aperture, thus improving visual acuity. Second, the width of the point spread function 51 (FIG. 2) for a truncated Gaussian apodization is broader than that for a uniform aperture (i.e., Airy Disk) when the truncated width of the Gaussian apodization is at the effective width of the Gaussian profile and equal to the width of the uniform aperture. FIG. 4 illustrates this effect by comparing the perfect lens modulation transfer function curve 3 (or contrast) of a uniform aperture to the modulation transfer function curve 5 of a truncated Gaussian apodized aperture. As can be seen, the contrast at low spatial frequencies for the truncated Gaussian apodized aperture is enhanced and suppressed at high spatial frequencies. However, the contrast at the high spatial frequencies for the truncated Gaussian apodized aperture can be increased by truncating the Gaussian apodized profile at a larger width.

Based on the principle discussed above, the inventive method produces a lens with pseudo-Gaussian apodized (or tapered) amplitude transmittance varying toward the edge of the aperture. The apodized aperture function is a pseudo-Gaussian profile 9 (FIG. 5) given by:

$$I(r) = e^{-(\frac{r}{c})^x}$$

where I(r), r, and c are defined above and $2 < x \leq 10$. The function is referred to as Gaussian when x=2 and as pseudo-Gaussian for values greater than 2. FIGS. 5–7 illustrate the effects of different values of x for the pseudo-Gaussian profile. For each of these figures, c equals 0.7 mm. The effective radius is chosen from the range of radii of a conventional pinhole contact lens, as discussed above, which is typically in the range of about 0.25 to 1.5 mm. In FIG. 5, profile 7 represents x=2 and profile 9 represents x=4. As can be seen in FIG. 5, increasing values of x produce a profile that is flatter in region 56 and steeper in region 58 than the Gaussian profile.

FIGS. 6 and 7 demonstrate the effects of pseudo-Gaussian profiles having different values for x. In FIG. 6, x equals 4 resulting in pseudo-Gaussian profile 60. In profile 60, the transmissivity is 100% until about 0.15 mm then gradually decreases to 20% transmissivity by about 0.79 mm and to 0% transmissivity by about 1.1 mm. In FIG. 7, x equals 10 resulting in pseudo-Gaussian profile 62. In profile 62, the transmissivity remains at 100% until about 0.4 mm, then steeply decreases to 20% transmissivity by about 0.75 mm and to 0% transmissivity by about 0.81 mm. The steep slope of profile 62 more closely simulates a conventional pinhole aperture without having the attendant diffraction problems. To provide for a multifocal effect, x is selected to provide minimal diffraction for a given patient relative to that patient's visual characteristics at the time of fitting, such is within the skill in the art. When x approaches very large numbers, the pseudo-Gaussian apodized aperture becomes essentially a uniform aperture.

To this point, the apodization has been described as a Gaussian or pseudo-Gaussian function, however, any number of functions can be used, such as, for example, linear, exponential, parabolic, combination thereof, to create the "soft edge." In addition, the present invention is not limited to "soft edges" that are defined by a mathematical function. It is within the scope of the invention that the "soft edge" be defined as any decreasing transmissivity that essentially begins at about 100% and decreases to about 20% or less within a distance in the range of about 0.05 mm or greater to about 1.0 mm or less, more preferably, decreases to about 10% or less within that distance, more preferably, decreases to about 1% or less within that distance. Likewise, more preferably decreases to about 20% or less within a distance in the range of about 0.1 mm or greater to about 1.0 mm or less, more preferably decreases to about 10% or less in that distance, more preferably decreases to about 1% or less in that distance. Likewise, more preferably decreases to about 20% or less within a distance in the range of about 0.15 mm or greater to about 0.4 mm or less, more preferably decreases to about 10% or less in that distance, more preferably decreases to about 1% or less in that distance. In these embodiments, the "soft edge" surrounds a clear aperture of a defined diameter in the range of about 1.0 to 2.0 mm, more preferably about 1.5 mm.

Referring to FIG. 8, a contact lens 10 that is fabricating by the present invention includes lens body 12 that has a first surface (not shown) optically configured (e.g., with a concave form) to conform to the eye curvature of the wearer. The lens body 12 has a second surface 16 optically configured (e.g., with a convex form) to correct the vision of the wearer selectively at a focus between and including far and near objects. Focusing is achieved both by the lens 10 and by the refractive capability of the wearer's eye. The contact lens has an annular mask 18 that is selectively transmissive along its inner edge 32 according to the principles discussed above to eliminate the sharp demarcation between the aperture 20 and the annular mask 18. The selective transmissivity along the inner edge 32 is achieved by starting with about 100% transmissivity at the junction with the aperture 20 and reducing the transmissivity radially outward until the aperture functions essentially like a pinhole aperture (i.e., opaque) even though there is no sharp demarcation at the transition from the clear aperture to the opaque mask. Preferably, in one embodiment, the mask is opaque at a transmissivity of about 1% or less. Preferably, the point at which the aperture functions essentially like a pinhole aperture is reached at a radial position of about 0.6 to 1 mm, more preferably about 0.6 to 0.8 mm, and most preferably at 0.7 mm. The transmissivity can continue to decrease beyond the point at which the aperture functions essentially like a pinhole aperture until the mask becomes opaque or the transmissivity can change quickly to essentially opaque or opaque for the remainder of the width of the mask such that it blocks light energy at the lens body 12. In this way, the annular mask 18 forms an essentially pinhole-like aperture 20 at the wearer's optical line-of-sight without diffraction effects generated by an abrupt edge. The variably transmissive aperture 20 is preferably arranged to be concentric with the wearer's line of sight, which could be off-center with respect to the geometric center of the lens.

Constructed in this fashion, the contact lens 10 operates similar to a pinhole imager and increases the depth of focus for objects viewed by the wearer. Normally, the typical geometrical vision deficiencies encountered in wearers, like myopia, hyperopia, astigmatism, and presbyopia, spread out the light rays reaching the retina from a single object point in the field of view, thereby reducing image contrast. The variably transmissive aperture 20 limits these light rays to a small bundle entering the eye pupil, and thereby improves image contrast. This lens has the further advantage over a conventional pinhole lens in that the "soft edge" reduces or eliminates diffraction, thus producing better visual acuity for the wearer.

The variably transmissive aperture 20 is sized to provide pinhole-like imaging improvement for the wearer's vision deficiency. The variably transmissive aperture 20 is smaller than the wearer's pupil size during average lighting conditions to improve vision clarity during such conditions. Preferably, however, the variably transmissive aperture 20 is smaller—or approximately equivalent to—the pupil of the wearer during bright light conditions. With this latter sizing, the wearer has improved vision clarity even during bright light conditions. The diameter of the variably transmissive aperture 20 is generally about 1 mm or greater and 2 mm or less. In a preferred embodiment, the variably transmissive aperture 20 is approximately 1.5 mm in diameter. Since the contact lens may not always center over the wearer's pupil, the lens 10 is preferably fitted first, and the position of the pupil noted, and the lens 10 is then made to special order according to the fitting so the annulus 18 centers over the wearer's pupil. Alternatively, the lens 10 can be mass-produced to meet a generalized population of wearer's or to meet a series of sets of wearer's requirements. In a preferred embodiment, the lens body 12 is weighted (e.g., with a prism ballast) or shaped to center the variably transmissive aperture 20 at the optimal location on the eye of the wearer, and to reduce the movement of the contact 10 on the wearer's eye, preferably to less than approximately one and one-half mm. Accordingly, the lens 10 is held in a relatively constant position on the eye of the wearer, thereby maximizing the lens 10 for central vision while reducing the possibility of a reduction in the peripheral field by decentering and other excessive movements.

In addition, the effective radius of the annular mask 18, from the soft edge 32 to the outside edge 26, is preferably approximately 0.65 mm or greater and 4.4 mm or less. This dimension is sized in the practice of the invention to accommodate the normal function of the human pupil.

The lens body 12 can be constructed with material to form a hard, gas permeable lens, or, alternatively, to form a soft contact lens (e.g., with a flexible soft polymer material). Combinations of these materials are also suitable to form a composite contact. The outer diameter of the lens body 12 is approximately 7 to 18 mm, depending upon the wearer's eye size. It can be appreciated that the dimensions of the annular mask 18 can be adjusted for a particular wearer. For example, the annular mask 18 can be sized for a particular pupil, or further optimized for a desired visual correction.

For ease of manufacture, the surface 16 away from the wearer's eye is appropriately configured and powered to correct the vision of the wearer for intermediate objects approximately midway between near and far objects. The contact lens 10 typically corrects the wearer's vision by forming an optical correction on the surface 16. Common corrections include convex, concave, toric, and astigmatic forms. Alternatively, or in conjunction with an optical correction on the surface 16, the surface in contact with the wearer's eye can similarly include an optical correction, such as a toric, astigmatic, or concave form. In a preferred embodiment, the portion of the surface 16 located in the variably transmissive aperture 20 is configured to correct the wearer's vision at an intermediate focus, and the portion of surface 16 located within the region 17 corrects the wearer's vision for far objects to provide a multi-powered lens. It should be apparent to those skilled in the art that other multi-powered corrections are possible.

The outer diameter of the annular mask 18 can be sized to be smaller than a wearer's dilated pupil during lower light conditions. During lower light conditions, the wearer can thus receive light rays at the retina through the transmitting region 17. Accordingly, the contact lens 10 increasingly transmits more light rays as the wearer's pupil size increases or dilates. The wearer is, therefore, better able to discern the same objects which were viewed under brighter conditions.

In another embodiment (FIG. 9A), the mask region 18 whether in the form of a coating or other structure, can have various selected levels of transmissivity. Opacity in the annular mask is generally desired for maximum visual sharpness. However, some wearers may want or need more light energy transmitted through the annular mask region 18 to avoid a sense of visual dimness or energy starvation (i.e., to attain more brightness) in medium to low light conditions. For example, the lens 10 (FIG. 9A) transmits less light energy towards the central portion 34 of the mask region 18 but still more than at the point of least transmissivity in the mask region and transmits relatively more light energy towards the outer edge 26 of the mask region than at the central portion 34 of the mask region 18. In one embodiment, the transmissivity transition for the annular mask 18 from less light energy to more light energy utilizes the Gaussian and/or pseudo-Gaussian principles discussed above to eliminate any sharp demarcation between the outer edge 26 and the clear region 17 to avoid adverse diffraction effects. As with the "soft edge" 32, the transmissivity in the annular mask region can follow any mathematical function or not be defined by a mathematical function. FIG. 10 illustrates the transmissivity for the lens of FIG. 9A. The transmissivity at the center of the lens starts at 100% then decreases according to the principles above until reaching a transmissivity below which the mask is opaque or performs as essentially opaque. Preferably, the transmissivity stays at that level for a width of between about 0.5 mm to 4 mm, preferably about 1.5 to 2 mm, to take full advantage of the benefits of the pinhole effect, then increases in transmissivity to the outer "soft edge" 26 or to the edge of the lens. Preferably, the transition in "soft edge" 32 is more rapid than the transition in the annular mask to its outer portion.

Currently, the tinted pattern on some conventional masked lenses have a clear demarcation between the opaque zone and the partially opaque or transparent zones. Under dim light conditions the iris of the wearer may be dilated to a pupil size greater than the opaque ring. This can create an annular window for forming a "structural halo" which may be visually disturbing. This is believed to be due to the defocused light passing through the annulus of the partially opaque ring or passing around the outer edge of the opaque ring on a conventional masked lens.

Lens fabrication by the present invention eliminates the halo by diminishing the distinct demarcation between the opaque and the partially opaque zones or at the outer edge of the opaque ring by radially "tapering" the opacity of the tinted pattern (FIG. 9B). The lens body 12 has a surface configured (e.g., with a concave form) to conform to the eye curvature of the wearer. The lens body 12 has a second surface 16 with a convex form. Optionally, the second surface 16 can be optically configured to correct the vision of the wearer selectively at a focus between and including far and near objects.

The present invention is also applicable to non-pinhole contact lens as illustrated herein. The contact lens 10 has an annular mask 18 of continuously variable transmissivity according to the particular needs of a given wearer. The annular mask 18 is arranged to form an aperture 20 at the wearer's optical line-of-sight. The aperture 20 is preferably arranged to be concentric with the wearer's pupil, which could be off-center with respect to the center of the lens body. The aperture 20 is sized to reduce peripheral aberrations and distortions while maximizing retinal illumination. In other words, the aperture is sized to correct optical aberrations with minimal energy starvation to the retina. The aperture is typically of a size greater than conventional "pinhole" contact lenses which produce refractive correction by reducing the retinal blur circle to allow for simultaneous focus of near and distance vision. Therefore, the aperture of the lens is of sufficient size so as not to be effective as or a substitute for refractive correction. Preferably, the diameter of the aperture is about 3.5 mm or larger, more preferably about 4 mm or larger, more preferably about 4.2 mm or larger for individuals having average sized pupils in medium light conditions. The size of the aperture is chosen to be as large as possible for a given wearer while still providing a mask region of sufficient size to treat the conditions described above. However, some individuals have paracentral corneal distortions, therefore, in some instances the aperture diameter may be about 2.0 mm or larger, preferably about 3.0 mm or larger, (which is within the range of conventional pinhole contact lens) but not be effective as or a substitute for refractive correction, such as for presbyopia.

In one embodiment (FIG. 9B), the mask region 18 whether in the form of a coating or other structure, can have various selected levels of transmissivity. Opacity in the annular mask is generally desired for maximum visual sharpness as visual dimness or energy starvation is generally not a problem with the present invention because the aperture diameter is sized so large relative to the wearer's pupil. However, some wearers may want or need more light energy transmitted through the annular mask region 18 to avoid a sense of visual dimness (i.e., to attain more brightness) in medium to low light conditions. For example, the lens 10 (FIG. 9B) transmits less light energy towards the central portion 34 of the mask region 18 and transmits relatively more light energy towards the outer edge 26 of the mask region. In one embodiment, the transmissivity transition for the annular mask 18 from less light energy to more light energy utilizes a Gaussian and/or pseudo-Gaussian function to eliminate any sharp demarcation at the edge of the mask region or between the outer edge 26 and any clear region that may exist if the mask region does not extend all the way to the outer region of the lens to avoid the adverse diffraction effects. The transmissivity in the annular mask region can follow any predetermined mathematical function or not be defined by a mathematical function.

In another embodiment, the tapered (progressive) mask pattern has a clear central aperture and the transmissivity of the mask increases gradually from 0% transmissivity at the edge of the clear central aperture to the periphery of the mask. The variation in transmissivity is symmetrical to the axis through the center of the aperture. The aperture 20 typically is greater than the diameter at which diffraction effects start to degrade image quality. In general, the benefits achieved can be destroyed by diffraction if small apertures relative to pupil size are incorporated into the lens. Such small apertures that have these adverse results include radial slits and scalloped patterns. Diffraction can actually increase the blurring of the retinal image such that the wearer's vision is degraded rather than improved. Thus, to maintain retinal illumination and reduce diffraction effects, typically the lower limit of an aperture in a usable contact lens is above about 3.5 mm, more preferably above about 4.0 mm, more preferably above about 4.2 mm.

In a further embodiment, the invention also produces a "soft edge" 32 at the junction of the clear aperture 20 and the annular mask 18. This can be accomplished by either reducing the transmittance of the central aperture as a function of increasing radial position, or by decreasing the transmissivity of the annular mask as a function of increasing radial position.

In yet another embodiment, the inventive process eliminates the sharp edge (i.e., abrupt demarcation) by apodizing the aperture. The transmittance function of the aperture 20 on lens 10 (FIG. 1) can be a Gaussian apodized aperture or pseudo-Gaussian apodized aperture described again by:

$$I(r) = e^{-\left(\frac{r}{c}\right)^x}$$

where I(r) is the transmissivity amplitude for the aperture 20 as a function of the radial position, r, and c is the effective radius of the aperture. The effective radius is of sufficient size to reduce peripheral aberrations and distortions but not to be effective as or a substitute for refractive correction. Preferably, the effective radius is in the range from about 2.0 to about 4.2 mm, and more preferably in the range from about 3.5 to about 4.0 mm, and x is chosen from the range $2 < x \leq 5$. The effective radius is chosen for a particular patient based on the type of optical distortion and the location of that distortion. For example, corneal topography can be utilized to identify the location and severity of keratoconus. Then, c would be chosen based on that location. The function is referred to as Gaussian when x equals 2 and as pseudo-Gaussian for values greater than 2 and preferably no more than 10.

As was in the case for the lens in FIG. 9A, any number of functions can be used to describe the apodization of the aperature of the lens in FIG. 9B. In addition, the present invention is not limited to "soft edges" that are defined by a mathematical function. It is within the scope of the invention that the "soft edge" be defined as any decreasing transmissivity that has diffraction-reducing effect as noted above.

For the lens of FIG. 9B, the transmissivity at the center of the lens starts at 100% then decreases according to the principles above until reaching a transmissivity below which the mask is opaque or performs as essentially opaque. Preferably, the transmissivity stays at that level for a width of between about 1 mm to about 4 mm, preferably about 1.5 to 2 mm, then increase in transmissivity to the outer "soft edge" 26 or to the edge of the lens. Preferably, the transition in "soft edge" 32 is more rapid than the transition through central portion 34 in the annular mask to its outer portion 26.

An optimal tapering profile of the opaque mask will be related to the pupil sizes and the retinal illumination required for the wearer. Since the lens may not always center over the wearer's pupil, the lens 10 is preferably fitted first, and the position of the annulus 18 noted, and the lens 10 then made to special order according to the fitting so the annulus 18 centers over the wearer's pupil. Alternatively, the lens can be mass-produced to fit a generalized population of wearers or to fit several sets of generalized wearers. In a preferred embodiment, the lens body 12 is weighted (e.g., with a prism ballast) or shaped to center the aperture 20 at the optimal location on the eye of the wearer, and to reduce the movement of the contact 10 on the wearer's eye, preferably to less than approximately one and one-half mm. Accordingly, the lens 10 is held in a relatively constant position on the eye of the wearer, thereby maximizing the lens 10 for central vision while reducing the possibility of a reduction in the peripheral field by decentering and other excessive movements.

In addition, the radial width of the annular mask 18, from the inside edge 32 to the outside edge 26, is preferably between about 0.95 mm or greater and about 4.5 mm or less. It will be appreciated that the annular mask can extend to the outside edge of the lens and thus its width would be determined by the diameter of the lens. The radial width is sized in the practice of the invention to accommodate the normal function of the human pupil while being effective in treating the above-listed conditions.

Fabrication of Lenses

The mask regions having variable transmissivity on the lens can be constructed in several ways. The inventive methods are applicable for fabricating "pinhole" and non-pinhole contact lenses. It is understood in describing the methods herein, the inventive techniques are not limited to the fabrication of any specific lens that is used for illustrative purposes.

In one method, an opaque spinning mask 44 (FIG. 11) is employed in the device illustrated diagrammatically in FIG. 12 to produce the annular mask shown in FIG. 8. This method can be used to produce a variably transmissive annular mask of any desirable profile depending on the pattern of the spinning mask used. A light source 40 and condenser lens 42 provide back illumination to mask 44 which is spun by motor 46. The spinning mask 44 as an object is imaged through relay lens 48 and imaging lens 50 onto the lens 10 using a photo-reactive dye or coating in or on the lens. Preferred photo-reactive dyes degrade upon exposure to radiation thereby permitting radiation visible (e.g., visible light) to transmit through a portion of the lens that was hitherto opaque. The opaque mask 44 has a central light transmitting region 52 and several light transmitting "petals" 54 extending radially outward from the region 52. The profile of the variably transmissive annular mask on the resulting lens is controlled by changing the shape of the design of the "petals". As the mask is spinning about an axis symmetric to the petal pattern, the image of the spinning mask becomes an apodized pattern on the lens with continuously variable gray tones. Suitable photo-reactive dyes are known and are described, for instance, in GB 1,547,525 which is incorporated herein.

Another technique, similar to that just described, utilizes a beamsplitter 60 as illustrated diagrammatically in FIG. 13, to combine the apodized aperture pattern with a second spinning mask 62 of any desirable pattern using another projection system branch. The beamsplitter can be, for example, a one-half silvered mirror. A tapered (i.e., reverse apodized) annular mask pattern is implemented in the second branch of the projection system to produce a masked lens as shown in FIGS. 9A and 9B having diffraction-reducing edges on the inside of the annular mask and the outside of the annular mask.

A mask 64 with a plurality of opaque petals 66 on a light-transmitting substrate disk 68 (FIG. 14A) is illuminated by a light source 70 and condenser lens 72 (FIG. 13). A magnified or demagnified image of the mask 64 is formed on the lens 10 by relay and imaging lenses 74, 76. As the mask 64 is spinning about an axis symmetric to the blade pattern, the image of the spinning mask becomes a brightness-tapered pattern with continuous gray tones. The brightness tapered profile of the image is controlled by the design of the shape of the petals. A second mask 62 of any desirable pattern, such as shown in FIG. 14B, is illuminated by a second light source 80 and condenser lens 82. A second magnified or demagnified image is formed on the lens 10 by relay and imaging lenses 84, 76 and beamsplitter 60. The final image is a combined image of the individual images superimposed on the lens 10. By controlling the brightness of the light sources and/or exposure time for each mask, a combined image of any desired transmissivity pattern can be produced in the lens.

In another method, a transparent dome 86 (FIG. 15) having a light-occluding portion 88 is used to produce the annular mask pattern in the lens. The dome (or support) 86 has a groove machined into the top of the dome beginning at a depth of about 0.1 mm deep in the region surrounding an area not machined out that will form the central aperture on the lens and rapidly increasing to a depth of about 1 mm at a diameter of about 1.6 mm then gradually decreasing to a depth of 0.1 mm at an outside diameter of 5.5 mm. The groove is filled with black blocking wax to form light occluding portion 88. As is apparent, the thickness of the wax forming the light occuling portion is not uniform, therefore, the amount of radiation penetrating through the wax will vary along the contour of the occlusion. In operation, lens 10 that has been emersed in a diazo dye solution (HD-61) and is placed on the dome 86 in position so that the light-occluding portion of the dome is in the position where the resulting annular mask should be on the finished lens. Light 90 is shone from beneath the dome until all exposed areas of the lens become discolored. The degree of discoloration at any point in the lens is proportional to the amount of radiation exposed thereto. A typical light source is a HA 6000 halogen ELH or ENX lamp. The lens is then placed into phloroglucinol solution in which the areas of the lens corresponding to the light-occluding part of the dome turn black and form a continually variable shade of gray resulting in an annular mask pattern such as shown in FIG. 9A.

In another method, the lens 10 is positioned on an opaque dome 92 in housing 98, and then contacted with a dam ring 94 to hold dye solution 96 (FIG. 16). Dye solution is placed in the dam ring and allowed to permeate the lens from the top side of the lens only. Dye is allowed to diffuse into the lens only to a depth necessary to produce the desired intensity, and not all the way through the thinnest section of the lens. Thereafter, the dam ring is removed and the dye rinsed off the surface quickly with water. A light restricting mask 100 is then placed over the lens 10 and the dye in the lens is desensitized by exposure to light (FIG. 17). The mask 100 is produced on a computer monitor with a commercially available graphics program. Then either printed out on a clear film or a slide is made with a 35 mm camera of the computer-generated mask pattern. The slide film is then used as the mask 100. Alternatively, the mask 100 can be produced by methods such as but not limited to selection of appropriate neutral density or color filters, metal deposition such as sputtering, vacuum deposition, printing, spraying, etc.

In order to achieve a more graduated or tapered edge, the mask can be raised slightly above the lens, so that a diffused edge will form from light diffracting effects. By varying the distance of the mask from the lens, the light intensity, duration of exposure to the light, and quality of light in the lens, different tapering effects may be produced in the lens.

As is evident, the device of FIGS. 16 and 17 can be employed to fabricated contact lens that has a circular central portion which is offset from the geometric center of the lens itself. One reason for the offset is that for most individuals, after the contacts lens has been placed on the cornea, movement of the contact lens causes the actual visual axis through the cornea to not coincide with the geometric axis of the lens. Offsetting compensates for this phenomenon so that the visual axis and geometric axis are aligned. Typically, the center of the central portion is offset a distance of about 0 mm to 1.5 mm. The requisite distance for an individual can be measured by conventional techniques prior to fabrication of the lens.

FIG. 18 depicts a device that is similar to the one illustrated in FIGS. 16 and 17 which is particularly suited for fabricating contact lens with a central portion which is offset from the geometric center of the contact lens. The devices includes a center dam 200, an inner ring 210, and an outer ring 220. The center dam has a diameter which is substantially equal to that of the pupil. In operation, a lens is positioned on the surface of dome 92 in housing 98. Thereafter, the center dam and the inner ring are placed in contact with the surface of the lens. A solution containing a vat dye in its leuco solubilized form is placed in contact with the surface of the lens that is bordered by the center dam and the inner ring. After a predetermined period of time has elapsed, the inner ring is lifted from the surface of the lens so that the vat dye solution now is in contact with a larger area of the lens surface that is bordered by the center dam and outer ring. In this fashion, more vat dye diffuses into the lens surface in the area adjacent to the center dam than in the area on the lens surface that is exposed upon lifting of the inner ring. Subsequently, the solution is removed and the lens is placed into a solution of sodium nitrite in dilute sulfuric acid whereupon the dye will precipitate out into the lens. The lens now contains a permanent dark color ring having a soft edge and the lens has a substantially clear center portion that is offset from the geometric center of the lens. Suitable vat dyes are described for example, in U.S. Pat. Nos. 4,898,695 and 5,534,038, which are incorporated herein.

Another technique employs a shutter-like mechanical device with several shutter blades arranged to provide masking in three concentric annular regions corresponding to the inner soft edge, the opaque portion and the outer soft edge as depicted in FIGS. 19A, 19B, 19C, and 19D. As shown in FIG. 19A, lens 158, that had been emersed in a diazo dye solution, is covered by a shutter system having a plurality of blades 125 (not all of which are shown) which initially blocks the passage of light onto the annular region defined by rings 151 and 154. In operation, as radiation is directed toward the lens, the shutter opens gradually as shown in FIGS. 19B and 19C until the shutter is in the opened position as shown in FIG. 19D. As is apparent, the lens region bordered by rings 152 and 153 remained covered and is not exposed to any radiation whereas the regions defined by rings 153 and 154 and by rings 151 and 152 are exposed to varying amounts of radiation. The regions on the lens that are exposed will discolor in proportion to the amount of radiation received. When the lens is placed into a phloroglucinol solution, the regions corresponding to the light-occluding part will turn black whereas the other regions will be clear or have variable levels of transparency. In this case, as shown in FIG. 19D, regions A and E will be substantially clear, regions B and D will exhibit a gradient in the levels of transparency, and region C will be substantially opaque. The opaque region will preferably have 1% transmissivity or less. The transmissivity of the inner soft edge and the outer soft edge can be varied, in part, by the speed of the shutter blades opening and with the shape of the shutter blades.

As is apparent, this technique can also be employed wherein the shutter blades are initially in the opened position and then gradually closed. Moreover, the sequence of exposing the dye to radiation and of opening and/or closing the shutter can be varied to generate different patterns of transmissivity in the contact lens. For instance, one portion of the shutter may be opening while another portion is simultaneously being closed.

A contact lens constructed in accordance with the invention is colored, tinted, or otherwise shaded, when appropriate, by methods known in the art. This coloring or tinting can be cosmetic, as it often is for many wearers of common contact lenses. It can also reduce the sometimes objectionable appearance of the annular mask 18 when viewed on the eye of the wearer. For example, the invention provides for an annulus that is matched to the wearer's iris. It also provides for an annulus that enhances or changes the appearance of the wearer's iris, if desired. A further enhancement can include a limbal ring as described in U.S. Pat. No. 5,302,978 which is incorporated herein.

It is understood that when employing dyes, the concentration of the dyes used can be varied (e.g., diluted) to achieve the desired degree of opaqueness and other related features.

It will be understood that changes may be made in the above constructions without departing from the scope of the invention. For example, the arrangement and size of the annular mask 18, can be selected for a particular wearer to optimize the visual correction available. In another example, the contact lens body 12 can be constructed with a yellow appearance, giving the wearer a physiological impression of brighter lighting. Those skilled in the art will appreciate that the invention can also aid wearers suffering from other vision deficiencies and disorders.

EXAMPLE 1

A contact lens in accordance with FIG. 9 was produced with the following procedure. A 1% sensitizer solution was formed by dissolving 1.0 grams of 4-diazo-[4'-toluyl]-mercapto-2,5-diethoxybenzene zinc chloride (also referred to as Diazo-15 or HD-61) in 100.0 grams of de-ionized water and sonicating for 15 to 20 minutes. A 1% developer solution was formed by dissolving 1.0 grams of phloroglucinol dihydrate in 100.0 grams of de-ionized water and sonicating for 15–20 minutes. The solutions were filtered using 0.45 micron filter paper prior to use. Prior to tinting, the lens was equilibrated in water for at least 1 hour. The lens was then pat dry and dropped in a vial containing about 6–8 mm of sensitizer. The front curve of the lens was uppermost. The lens was left in the solution for 3 minutes. The lens was removed, rinsed with water and pat dry. The lens was positioned on a dome and the imaging mask pattern placed over the lens on the dome. The dome was then placed over a type ENX HA 6000 Halogen light source for 2 minutes. The lens was then removed from the dome and placed in the developer solution for 2 minutes. The lens was then rinsed with clean water and processed via the usual extraction and hydration processes.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A method of fabricating a lens adapted to be worn on or implanted in the eye wherein the lens includes regions having different levels of visible light transmissivity, that comprises the steps of:
   a. positioning a lens substrate onto a first surface of a substrate support wherein a photosensitive reagent is present on a lens substrate surface, in the lens surface, or in both the lens substrate surface and the lens surface and wherein the second surface of the support comprises radiation restricting regions;
   b. directing radiation through the second surface of the support and onto the lens substrate; and
   c. exposing the lens substrate to sufficient radiation to cause the photosensitive reagent to react whereby the lens fabricated has an annular mask region surrounding a central portion having selected transmissivity such that the central portion transmits more light energy at the center of the central portion and less light energy toward an outer edge of the annular mask region without demarcation in the change in transmissivity within the annular mask region and wherein the central portion has a diameter of sufficient size as not to be effective as or a substitute for refractive correction wherein the lens that is fabricated has a substantially transparent central portion that has a center which is offset from the geometric center of the lens.

2. The method of claim 1 wherein the center of the substantially transparent central portion is offset by a distance of up to about 1.5 mm from the geometric center.

3. The method of claim 1 wherein the central portion is substantially clear and the annular mask region is substantially opaque.

4. A method of fabricating a lens adapted to be worn on or implanted in the eye wherein the lens includes regions having different levels of visible light transmissivity, that comprises the steps of:
   a. providing a lens substrate that has a photosensitive reagent present on the lens substrate surface or in the lens substrate;
   b. positioning a mask having radiation restricting regions over a surface of the lens substrate;
   c. providing a source of radiation and directing radiation through the mask and onto the lens substrate;
   d. exposing the lens substrate to sufficient radiation to interact with the photosensitive reagent whereby the lens fabricated has an annular mask region surrounding a central portion having selected transmissivity such that the central portion transmits more light energy at the center of the central portion and less light energy toward an outer edge of the annular mask region without demarcation in the change in transmissivity within the annular mask region and wherein the central portion has a diameter of sufficient size so as not to be effective as or a substitute for refractive correction; and
   e. rotating the mask.

5. The method of claim 4 further comprising the step of positioning one or more optical lenses between the source of radiation and the mask to focus radiation onto the mask.

6. The method of claim 4 further comprising the step of positioning one or more optical lenses to focus radiation that has passed through the mask onto the lens substrate.

7. The method of claim 4 wherein the central portion is substantially clear and the annular mask region is substantially opaque.

8. A method of fabricating a lens adapted to be worn on or implanted in the eye wherein the lens includes regions having different levels of visible light transmissivity, that comprises the steps of:
   a. providing a lens substrate that has a photosensitive reagent present on a lens substrate surface or in the lens surface;
   b. providing a first source of radiation and positioning adjacent to said first source a first mask having first radiation restricting regions;
   c. providing a second source of radiation and positioning adjacent to said second source a second mask having second radiation restricting regions;
   d. focusing radiation from the first source onto the lens substrate whereby the radiation travels through the first mask;
   e. focusing radiation from the second source onto the lens substrate whereby the radiation travels through the second mask; and
   f. exposing the lens substrate to sufficient radiation to react with the photosensitive reagent whereby the lens fabricated has an annular mask region surrounding a central portion having selected transmissivity such that the central portion transmits more light energy at the center of the central portion and less light energy toward an outer edge of the annular mask region without demarcation in the change in transmissivity within the annular mask region and wherein the central portion has a diameter of sufficient size as not to be effective as or a substitute for refractive correction wherein the lens that is fabricated has a substantially transparent central portion that has a center which is offset from the geometric center of the lens.

9. The method of claim 8 further comprising the step of rotating one or both of said first and second masks.

10. The method of claim 8 wherein radiation from the first source and radiation from the second source travel through a beam splitter to produce a beam of radiation that is directed at the lens substrate.

11. The method of claim 8 wherein the center of the substantially transparent central portion is offset by a distance of up to about 1.5 mm from the geometric center.

12. A method of fabricating a lens adapted to be worn on or implanted in the eye wherein the lens includes regions having different levels of visible light transmissivity, that comprises the steps of:
   a. providing a lens substrate that has a photosensitive reagent present on the lens substrate surface or in a lens substrate;
   b. providing a source of radiation;
   c. positioning a shutter masking device between the source of radiation and said lens surface; and
   d. opening a shutter window in the device from a first position to second position as radiation is directed onto the surface of the substrate through the window thereby exposing a surface of the lens substrate to varying levels of radiation and causing the photosensitive reagent to react and produce a light transmissivity gradient in said lens substrate whereby the lens fabricated has an annular mask region surrounding a central portion having selected transmissivity such that the central portion transmits more light energy at the center of the central portion and less light energy toward an outer edge of the annular mask region without demarcation in the change in transmissivity within the annular mask region and wherein the central portion has a diameter of sufficient size as not to be effective as or a substitute for refractive correction wherein the lens that is fabricated has a substantially transparent central portion that has a center which is offset from the geometric center of the lens.

13. The method of claim 12 wherein the center of the substantially transparent central portion is offset by a distance of up to about 1.5 mm from the geometric center.

14. The method of claim 12 in which the central portion is substantially clear and the annular mask region is substantially opaque.

15. A method of fabricating a lens adapted to be worn on or implanted in the eye wherein the lens includes regions having different levels of visible light transmissivity, that comprises the steps of:
   a. providing a lens substrate that has a photosensitive reagent present on the lens substrate surface or in a lens substrate;
   b. providing a source of radiation;
   c. positioning a shutter masking device between the source of radiation and said lens surface;
   d. directing radiation towards the device; and
   e. closing a shutter window in the device from a first position to second position as radiation is directed onto the surface of the substrate through the window thereby exposing a surface of the lens substrate to varying levels of radiation and causing the photosensitive reagent to react and produce a light transmissivity gradient in said lens substrate whereby the lens fabricated has an annular mask region surrounding a central portion having selected transmissivity such that the central portion transmits more light energy at the center of the central portion and less light energy toward an outer edge of the annular mask region without demarcation in the change in transmissivity within the annular mask region and wherein the central portion has a diameter of sufficient size as not to be effective as or a substitute for refractive correction wherein the lens that is fabricated has a substantially transparent central portion that has a center which is offset from the geometric center of the lens.

16. The method of claim 15 wherein the center of the substantially transparent central portion is offset by a distance of up to about 1.5 mm from the geometric center.

17. The method of claim 15 in which the central portion is substantially clear and the annular mask region is substantially opaque.

18. A method of fabricating a lens adapted to be worn on or implanted in the eye wherein the lens includes regions having different levels of visible light transmissivity, that comprises the steps of:
   a. providing a lens substrate that has a photosensitive reagent present on the lens substrate surface or in the lens substrate;
   b. positioning a mask having radiation restricting regions over a surface of the lens substrate;
   c. providing a source of radiation and directing radiation through the mask and onto the lens substrate; and
   d. exposing the lens substrate to sufficient radiation to interact with the photosensitive reagent whereby the lens fabricated has an annular mask region surrounding a central portion having selected transmissivity such that the central portion transmits more light energy at the center of the central portion and less light energy toward an outer edge of the annular mask region without demarcation in the change in transmissivity within the annular mask region wherein the central portion has a diameter of sufficient size so as not to be effective as or a substitute for refractive correction and wherein the lens that is fabricated has a substantially transparent central portion that has a center which is offset from the geometric center of the lens.

19. The method of claim 18 wherein the center of the substantially transparent central portion is offset by a distance of up to about 0 mm to 1.5 mm from the geometric center.

* * * * *